United States Patent
Weston et al.

(10) Patent No.: US 8,308,714 B2
(45) Date of Patent: Nov. 13, 2012

(54) CONTROL CIRCUIT AND METHOD FOR NEGATIVE PRESSURE WOUND TREATMENT APPARATUS

(75) Inventors: Richard Scott Weston, Carlsbad, CA (US); Tianning Xu, San Antonio, TX (US)

(73) Assignee: Bluesky Medical Group Inc., Memphis, TN (US)

( * ) Notice: Subject to any disclaimer, the term of this patent is extended or adjusted under 35 U.S.C. 154(b) by 648 days.

(21) Appl. No.: 12/445,043

(22) PCT Filed: Oct. 12, 2007

(86) PCT No.: PCT/US2007/021790
§ 371 (c)(1),
(2), (4) Date: Apr. 9, 2009

(87) PCT Pub. No.: WO2008/048481
PCT Pub. Date: Apr. 24, 2008

(65) Prior Publication Data
US 2010/0100075 A1 Apr. 22, 2010

Related U.S. Application Data

(60) Provisional application No. 60/851,663, filed on Oct. 13, 2006.

(51) Int. Cl.
*A61M 27/00* (2006.01)
(52) U.S. Cl. .......................... 604/543; 604/541
(58) Field of Classification Search .................. 604/543, 604/540
See application file for complete search history.

(56) References Cited

U.S. PATENT DOCUMENTS

| 4,271,701 A | * | 6/1981 | Dempster et al. ........... 73/861.42 |
| 4,316,466 A | | 2/1982 | Babb |
| 4,321,552 A | * | 3/1982 | Franssen et al. ................. 330/81 |

(Continued)

FOREIGN PATENT DOCUMENTS

CA 2198243 A1 2/1996

(Continued)

OTHER PUBLICATIONS

Bagautdinov, "Variant of External Vacuum Aspiration in the Treatment of Purulent Diseases of Soft Tissues," Current Problems in Modern Clinical Surgery, 1986, 4 pages.

(Continued)

*Primary Examiner* — Susan Su
(74) *Attorney, Agent, or Firm* — Knobbe Martens Olson & Bear LLP

(57) ABSTRACT

A negative pressure wound therapy apparatus can include a wound dressing, a fluid collection container, a vacuum pump comprising a pump motor, and tubing. Additionally, the apparatus can include a pressure sensor that measures a pressure in the tubing. One or more tubes can channel a fluid between the wound dressing, the fluid collection canister, and the pump. In addition, first and second control circuits can be provided for controlling the pump motor without using a processor. The first control circuit can generate a difference signal between a desired pressure input and a pressure sensor input, and can further generate a motor control signal responsive to the difference signal. Moreover, a second control circuit can provide an override signal based at least in part on the difference signal and at least one reference signal. The override signal beneficially overrides the motor control signal to prevent the pump motor from stalling.

25 Claims, 13 Drawing Sheets

U.S. PATENT DOCUMENTS

| | | | |
|---|---|---|---|
| 4,382,441 A | 5/1983 | Svedman | |
| 4,710,165 A | 12/1987 | McNeil et al. | |
| 4,740,202 A | 4/1988 | Stacey et al. | |
| 4,795,448 A | 1/1989 | Stacey et al. | |
| 4,969,880 A | 11/1990 | Zamierowski | |
| 4,979,944 A | 12/1990 | Luzsicza | |
| 5,002,539 A | 3/1991 | Coble et al. | |
| 5,356,378 A * | 10/1994 | Doan | 604/65 |
| 5,390,021 A * | 2/1995 | Nagata et al. | 356/461 |
| 5,419,768 A | 5/1995 | Kayser | |
| 5,429,601 A | 7/1995 | Conley et al. | |
| 5,449,347 A | 9/1995 | Preen et al. | |
| 5,549,584 A | 8/1996 | Gross | |
| 5,623,936 A * | 4/1997 | McClure | 600/518 |
| 5,636,643 A | 6/1997 | Argenta et al. | |
| 5,637,093 A | 6/1997 | Hyman et al. | |
| 5,645,081 A | 7/1997 | Argenta et al. | |
| 6,135,116 A | 10/2000 | Vogel et al. | |
| 6,142,982 A | 11/2000 | Hunt et al. | |
| 6,159,160 A | 12/2000 | Hsei et al. | |
| 6,229,286 B1 | 5/2001 | Tokuyama | |
| 6,368,311 B1 | 4/2002 | Valerio et al. | |
| 6,458,109 B1 | 10/2002 | Henley et al. | |
| 6,695,823 B1 | 2/2004 | Lina et al. | |
| 6,764,462 B2 | 7/2004 | Risk, Jr. | |
| 6,824,533 B2 | 11/2004 | Risk, Jr. | |
| 6,868,739 B1 | 3/2005 | Krivitski et al. | |
| 6,951,553 B2 | 10/2005 | Bubb et al. | |
| 7,004,915 B2 | 2/2006 | Boynton et al. | |
| 7,022,113 B2 | 4/2006 | Lockwood et al. | |
| 7,092,797 B2 | 8/2006 | Gaines et al. | |
| 7,108,683 B2 | 9/2006 | Zamierowski | |
| 7,128,735 B2 | 10/2006 | Weston | |
| 7,160,273 B2 | 1/2007 | Greter et al. | |
| 7,216,651 B2 | 5/2007 | Argenta et al. | |
| 7,438,705 B2 | 10/2008 | Karpowicz et al. | |
| 7,494,482 B2 | 2/2009 | Orgill et al. | |
| 7,553,306 B1 * | 6/2009 | Hunt et al. | 604/543 |
| 7,611,500 B1 | 11/2009 | Lina et al. | |
| 7,708,724 B2 | 5/2010 | Weston | |
| 7,776,028 B2 | 8/2010 | Miller et al. | |
| 7,790,945 B1 | 9/2010 | Watson, Jr. | |
| 7,811,269 B2 | 10/2010 | Boynton et al. | |
| 7,846,141 B2 | 12/2010 | Weston | |
| 7,909,805 B2 | 3/2011 | Weston | |
| 7,927,319 B2 | 4/2011 | Lawhorn | |
| 2002/0156464 A1 | 10/2002 | Blischak et al. | |
| 2002/0161346 A1 | 10/2002 | Lockwood et al. | |
| 2002/0183702 A1 | 12/2002 | Henley et al. | |
| 2002/0198503 A1 | 12/2002 | Risk et al. | |
| 2002/0198504 A1 | 12/2002 | Risk et al. | |
| 2003/0014022 A1 | 1/2003 | Lockwood et al. | |
| 2003/0040687 A1 | 2/2003 | Boynton et al. | |
| 2003/0097100 A1 | 5/2003 | Watson | |
| 2003/0108587 A1 | 6/2003 | Orgill et al. | |
| 2004/0073151 A1 | 4/2004 | Weston | |
| 2004/0167482 A1 | 8/2004 | Watson | |
| 2005/0029976 A1 | 2/2005 | Terry et al. | |
| 2005/0166683 A1 | 8/2005 | Krivitski et al. | |
| 2005/0203452 A1 | 9/2005 | Weston | |
| 2005/0222527 A1 | 10/2005 | Miller et al. | |
| 2005/0222528 A1 | 10/2005 | Weston | |
| 2005/0222544 A1 | 10/2005 | Weston | |
| 2005/0261615 A1 | 11/2005 | Weston | |
| 2005/0261642 A1 | 11/2005 | Weston | |
| 2006/0025727 A1 | 2/2006 | Boehringer et al. | |
| 2006/0129137 A1 | 6/2006 | Lockwood et al. | |
| 2007/0014837 A1 | 1/2007 | Johnson et al. | |
| 2007/0016152 A1 * | 1/2007 | Karpowicz et al. | 604/326 |
| 2007/0032763 A1 | 2/2007 | Vogel | |
| 2007/0055209 A1 | 3/2007 | Patel et al. | |
| 2007/0118096 A1 | 5/2007 | Smith et al. | |
| 2007/0219532 A1 | 9/2007 | Karpowicz et al. | |
| 2007/0239139 A1 | 10/2007 | Weston et al. | |
| 2008/0071216 A1 | 3/2008 | Locke et al. | |
| 2008/0071234 A1 | 3/2008 | Kelch et al. | |
| 2008/0200857 A1 | 8/2008 | Lawhorn | |
| 2008/0200906 A1 | 8/2008 | Sanders et al. | |
| 2008/0234641 A1 | 9/2008 | Locke et al. | |
| 2008/0281281 A1 | 11/2008 | Meyer et al. | |
| 2009/0163882 A1 | 6/2009 | Koch et al. | |
| 2010/0036367 A1 | 2/2010 | Krohn | |
| 2010/0042074 A1 | 2/2010 | Weston et al. | |
| 2010/0185164 A1 | 7/2010 | Hartwell et al. | |
| 2010/0207768 A1 | 8/2010 | Pidgeon et al. | |
| 2010/0211030 A1 | 8/2010 | Turner et al. | |
| 2010/0211031 A1 | 8/2010 | Hartwell | |
| 2010/0249691 A1 * | 9/2010 | Van Der Mooren et al. | 604/9 |
| 2010/0278518 A1 | 11/2010 | Gordon et al. | |
| 2010/0298792 A1 | 11/2010 | Weston et al. | |
| 2011/0008179 A1 | 1/2011 | Turner et al. | |
| 2011/0028921 A1 | 2/2011 | Hartwell et al. | |
| 2011/0071483 A1 | 3/2011 | Gordon et al. | |
| 2011/0130730 A1 | 6/2011 | Hartwell et al. | |
| 2011/0172616 A1 | 7/2011 | Hartwell et al. | |
| 2011/0251569 A1 * | 10/2011 | Turner et al. | 604/318 |
| 2012/0078539 A1 | 3/2012 | Vernon-Harcourt et al. | |

FOREIGN PATENT DOCUMENTS

| | | |
|---|---|---|
| CA | 2237606 A1 | 5/1997 |
| CA | 2551340 A1 | 5/1997 |
| CA | 2458285 A1 | 3/2003 |
| CA | 2483654 A1 | 11/2003 |
| DE | 1963258 | 6/1971 |
| DE | 4016034 A1 | 11/1991 |
| DE | 195 17 699 | 11/1996 |
| DE | 10 2005 014420 A1 | 9/2006 |
| EP | 0 194 198 A | 9/1986 |
| EP | 0 194 198 A2 | 9/1986 |
| EP | 0 194 198 A3 | 9/1986 |
| EP | 1 088 569 A | 4/2001 |
| EP | 1 897 569 B1 | 8/2002 |
| GB | 2047438 A | 3/1980 |
| GB | 2235877 A | 9/1989 |
| GB | 2 307 180 A | 5/1997 |
| GB | 2342584 A | 4/2000 |
| GB | 2 356 148 A | 5/2001 |
| GB | 2418738 | 4/2006 |
| WO | WO 96/05873 | 2/1996 |
| WO | WO 00/21586 | 4/2000 |
| WO | WO 01/37922 A2 | 5/2001 |
| WO | WO 01/37922 A3 | 5/2001 |
| WO | WO 03/005943 | 1/2003 |
| WO | WO 03/92620 | 11/2003 |
| WO | WO 03/101508 A2 | 12/2003 |
| WO | WO 2005/115497 | 12/2005 |
| WO | WO 2006/052745 A2 | 5/2006 |
| WO | WO 2006/052745 A3 | 5/2006 |
| WO | WO 2006/135934 | 12/2006 |
| WO | WO 2007/013064 | 2/2007 |
| WO | WO 2007/019038 A | 2/2007 |
| WO | WO 2007/030599 | 3/2007 |
| WO | WO 2007/062024 | 5/2007 |
| WO | WO 2007/088530 A | 8/2007 |
| WO | WO 2008/010094 | 1/2008 |
| WO | WO 2008/030872 | 3/2008 |
| WO | WO 2008/036360 | 3/2008 |
| WO | WO 2008/036361 | 3/2008 |
| WO | WO 2008/039223 | 4/2008 |
| WO | WO 2008/039314 | 4/2008 |
| WO | WO 2007/088530 | 8/2008 |
| WO | WO 2009/019415 | 2/2009 |
| WO | WO 2009/019496 | 2/2009 |

OTHER PUBLICATIONS

International Preliminary Report on Patentability for PCT/US2007/021790, mailed Apr. 23, 2009, in 14 pages.

International Search Report and Written Opinion, International Application No. PCT/US07/021790, dated Jul. 21, 2008, in 22 pages.

Jeter, Katherine F. ET, Managing Draining Wounds and Fistulae: New and Established Methods, Chronic Wound Care, Chapter 27, pp. 240-246, 1990.

Info V.A.C. User Manual—KCI—Dec. 2006 (76 pages).

Landis, E.M. and J.H. Gibbon, Jr., The Effects of Alternate Suction and Pressure on Blood Flow to the Lower Extremities, Alternate Suction and Pressure, J Clin Invest. Sep. 1933, 12(5):925-961.

Nursing75, Wound Suction: Better Drainage with Fewer Problems: Oct. 1975—vol. 5—Issue 10—p. 52-55.

US Medco Healthcare, Healing through Technology, HYPOwound Therapy System, from website http://www.usmedco.net. Downloaded from internet Apr. 18, 2006.

International Search Report from PCT/GB2008/050511, mailed Oct. 31, 2008 in 4 pages.

Written Opinion from PCT/GB2008/050511, mailed Feb. 9, 2010 in 6 pages.

European Search report dated Mar. 8, 2012 received in European Application No. EP 11 01 0128 in 9 pages.

* cited by examiner

CONTROL CIRCUIT AND METHOD FOR NEGATIVE PRESSURE WOUND TREATMENT APPARATUS

CROSS-REFERENCE TO RELATED APPLICATIONS

This application is a U.S. National Phase of the PCT International Application No. PCT/US2007/021790, filed on 12 Oct. 2007, which claims priority to a U.S. Provisional Patent Application No. 60/851,663, filed on 13 Oct. 2006. The disclosure of both prior applications is incorporated by reference in their entirety and should be considered a part of this specification.

BACKGROUND

1. Technical Field

Certain embodiments of the present application relate to treating a wound by applying reduced or negative pressure to the wound.

2. Description of the Related Art

The treatment of open or chronic wounds that are too large to spontaneously close or otherwise fail to heal has long been a troublesome area of medical practice. Closure of an open wound requires inward migration of surrounding epithelial and subcutaneous tissue. Some wounds, however, are sufficiently large or infected that they are unable to heal spontaneously. In such instances, a zone of stasis in which localized edema restricts the flow of blood to the epithelial and subcutaneous tissue forms near the surface of the wound. Without sufficient blood flow, the wound is unable to successfully fight bacterial infection and is accordingly unable to close spontaneously.

An initial stage of wound healing is characterized by the formation of granulation tissue which is a matrix of collagen, fibronectin, and hyaluronic acid carrying macrophages, fibroblasts, and neovasculature that forms the basis for subsequent epithelialization of the wound. Infection and poor vascularization hinder the formation of granulation tissue within wounded tissue, thereby inhibiting wound healing. It therefore becomes desirable to provide a technique for increasing blood circulation within wounded tissue to promote spontaneous healing and to reduce infection.

Another problem encountered during the treatment of wounds is the selection of an appropriate technique for wound closure during the healing process. Sutures are often used to apply force to adjacent viable tissue in order to induce the edges of a wound to migrate together and heal. However, sutures apply a closure force to only a very small percentage of the area surrounding a wound. When there is scarring, edema, or insufficient tissue, the tension produced by the sutures can become great causing excessive pressure to be exerted by the sutures upon the tissue adjacent to each suture. As a result, the adjacent tissue often becomes ischemic thereby rendering suturing of large wounds counterproductive. If the quantity or size of the sutures is increased to reduce the tension required of any single suture, the quantity of foreign material within the wound is concomitantly increased and the wound is more apt to become infected. Additionally, the size or type of a particular wound may prevent the use of sutures to promote wound closure. It therefore becomes desirable to provide an apparatus and method for closing a large wound that distributes a closure force evenly about the periphery of the wound.

Wounds resulting from ischemia, or lack of blood flow, are also often difficult to heal since decreased blood flow to a wound may inhibit normal immune reaction to fight infection. Patients that are bedridden or otherwise non-ambulatory are susceptible to such ischemic wounds as decubitus ulcers or pressure sores. Decubitus ulcers form as a result of constant compression of the skin surface and underlying tissue thus restricting circulation. Since the patient is often unable to feel the wound or to move sufficiently to relieve the pressure, such wounds can become self-perpetuating. Although it is common to treat such wounds with flaps, the conditions that initially caused the wound may also work against successful flap attachment. Wheelchair-bound paraplegics, for example, must still remain seated after treatment of pelvic pressure sores. It therefore becomes desirable to provide a treatment procedure for ischemic wounds that can be conducted in situ upon an immobile or partially mobile patient.

Other types of wounds in which ischemia leads to progressive deterioration include partial thickness burns. A partial thickness burn is a burn in which the cell death due to thermal trauma does not extend below the deepest epidermal structures such as hair follicles, sweat glands, or sebaceous glands. The progression of partial thickness burns to deeper burns is a major problem in burn therapy. The ability to control or diminish the depth of burns greatly enhances the prognosis for burn patients and decreases morbidity resulting from burns. Partial thickness burns are formed of a zone of coagulation, which encompasses tissue killed by thermal injury, and a zone of stasis. The zone of stasis is a layer of tissue immediately beneath the zone of coagulation. Cells within the zone of stasis are viable, but the blood flow is static because of collapse of vascular structures due to localized edema. Unless blood flow is re-established within the zone of stasis soon after injury, the tissue within the zone of stasis also dies. The death of tissue within the zone of stasis is caused by lack of oxygen and nutrients, reperfusion injury (re-establishment of blood flow after prolonged ischemia), and decreased migration of white blood cells to the zone resulting in bacterial proliferation. Again, it becomes desirable to provide a technique for treating burn wounds by enhancing blood circulation to the wounded tissue to inhibit burn penetration.

There exist various apparatus utilizing reduced pressure for treatment of these types of wounds. However, the existing apparatus do not have adequate means to monitor the pressure in the area of the wound beneath the cover. If the cover is not adequately sealed to the tissue surrounding the wound, reduced pressure cannot be maintained beneath the cover so that the benefits of the treatment are lost or diminished. In addition, pressure leaks through the seal cause the source of suction to operate more frequently, which consumes more energy and causes the suction equipment to wear faster than it would otherwise, reducing its useful life. Further, the flow of air into the wound area as a result of such leaks can result in increased risk of infection and intrusion of other harmful foreign material into the wound area. It is therefore desirable to have a relatively inexpensive means of monitoring the pressure level beneath the cover at the site of the wound, and to have a pressure sensor configuration that can detect the magnitude of the leak in the seal and warn the operator of the system when a certain threshold magnitude has been exceeded.

SUMMARY OF THE INVENTION

Certain embodiments described herein are directed to systems, methods and apparatuses for wound therapy. However, it will be appreciated that the systems, methods and apparatuses may have application to other fields. In certain preferred embodiments, the wounds being treated may include, but are not limited to, acute and chronic wounds, orthopedic trauma wounds, and post-Cesarean wounds, to name a few.

In some embodiments, such wounds are treated using a negative pressure wound therapy apparatus preferably comprising a wound dressing, a fluid collection container, a vacuum pump comprising a pump motor, and tubing. In addition, in some embodiments, the apparatus can include a pressure sensor that measures a pressure in the tubing. In some embodiments, one or more tubes of the tubing can channel a fluid between the wound dressing, the fluid collection canister, and the pump. In addition, in some embodiments, first and second control circuits can be provided for controlling the pump motor without using a processor. In some embodiments, the first control circuit can generate a difference signal between a desired pressure input and a pressure sensor input, and can further generate a motor control signal responsive to the difference signal. Moreover, in some embodiments, a second control circuit can provide an override signal based at least in part on the difference signal and at least one reference signal. In some embodiments, the override signal preferably beneficially overrides the motor control signal to prevent the pump motor from stalling.

In some embodiments, such wounds are treated using a negative pressure wound therapy apparatus preferably comprising a wound dressing, a fluid collection container, a vacuum pump comprising a pump motor, one or more tubes, a pressure sensor configured to measure a pressure in one or more of said one or more tubes and to generate a pressure sensor signal, a first control circuit to control the pump motor without using a processor, and a second control circuit. In some embodiments, the tubes are preferably configured to at least channel a flow of fluid between the wound dressing, the fluid collection canister, and the pump. In some embodiments, the first control circuit is preferably configured to generate a difference signal comprising a difference between a desired pressure input and the pressure sensor signal from the pressure sensor, and to generate a motor control signal responsive to the difference signal. The motor control signal is preferably configured to control the speed of the pump motor. The second control circuit is preferably configured to provide, without using a processor, an override signal to prevent the pump motor from stalling. In some embodiments, the override signal is preferably based at least in part on the difference signal and at least one reference signal, the override signal preferably being configured to override the motor control signal and thereby prevent the pump motor from stalling.

In some embodiments, the second control circuit in the apparatus described above provides the override signal by comparing the difference signal to the at least one reference signal. In some embodiments, the desired pressure input in the apparatus described above is provided by a user. In some embodiments, the second control circuit in the apparatus described above comprises a comparison circuit in communication with an AND gate. In some embodiments, the apparatus described above further comprises a high pressure cut-off circuit configured to override the first and second control circuits when the output signal from the pressure sensor exceeds a predetermined value. In some embodiments, the apparatus described above further comprises an intermittent delay circuit configured to reduce a duty cycle of the pump motor. In some embodiments, the first control circuit in the apparatus described above comprises a difference amplifier in communication with a pulse width modulator. In some embodiments, the difference amplifier generates the difference signal and the pulse width modulator generates the motor control signal.

In some embodiments, such wounds are treated using a negative pressure wound therapy apparatus preferably comprising a wound dressing, a fluid collection container, a vacuum pump preferably comprising a pump motor, one or more tubes configured to at least channel a flow of fluid between the wound dressing, the fluid collection canister, and the pump, a pressure sensor configured to measure a pressure in one or more of said one or more tubes and to generate a pressure sensor voltage reflecting the pressure in one or more of said one or more tubes, and a control circuit for controlling the pressure in the one or more tubes without using a processor. In this embodiment, the control circuit preferably comprises a pressure controller for controlling the pump motor, a pulse width modulator, and a stall controller for preventing stalling of the pump motor. Further, the pressure controller preferably comprises a difference circuit configured to receive the pressure sensor voltage, a desired pressure voltage from a user, and to provide a difference signal comprising an amplified difference between the desired pressure voltage and the pressure sensor voltage, wherein the difference circuit provides proportional control. Further, the pulse width modulator is preferably configured to generate a motor control signal responsive to the difference signal.

In some embodiments, the motor control signal is preferably used to control the speed of the pump motor. In some embodiments, the stall controller is preferably configured to prevent stalling of the pump motor and preferably comprises a comparison circuit and stall logic. The comparison circuit of some embodiments is preferably configured to generate an override signal, configured to prevent stalling of the pump motor, based at least in part on the difference signal and at least one reference signal. The stall logic of this embodiment is preferably configured to output a combined control signal based at least in part on the override signal and the motor control signal, the combined control signal configured to control the pressure in the one or more tubes without stalling the pump motor.

In some embodiments, the pressure sensor in the apparatus described above is preferably positioned such that it is in communication with the flow of fluid between the container and the pump. In some embodiments, the comparison circuit in the apparatus described above preferably generates the override signal by comparing the difference signal to the at least one reference signal. In some embodiments, the pressure sensor in the apparatus described above is preferably secured to the control circuit. In some embodiments, the difference circuit in the apparatus described above preferably controls a duty cycle of the pulse width modulator. In some embodiments, the difference circuit in the apparatus described above preferably comprises an operational amplifier. In some embodiments, the stall logic in the apparatus described above comprises an AND gate.

In some embodiments, a method of controlling a pump for negative pressure wound therapy for treatment of wounds is provided. In some embodiments, the method comprises the steps of providing a wound dressing, a fluid collection container, a vacuum pump, a pressure sensor configured to measure a pressure in the one or more tubes and to generate an output signal, and one or more tubes configured to at least channel a flow of fluid between the wound dressing, the fluid collection canister, and the pump. In some embodiments, the method also comprises the steps of providing a motor control signal without using a processor and preventing stalling of the pump motor. In some embodiments, the step of providing the motor control signal comprises the steps of receiving the output signal from the pressure sensor, providing a difference signal comprising a difference between a desired pressure input and the output signal from the pressure sensor, and generating a motor control signal responsive to the difference signal, the motor control signal configured to control the pump motor. In some embodiments, the step of preventing stalling of the pump motor comprises the steps of generating an override signal based at least in part on the difference signal and at least one reference signal, and preventing the pump motor from stalling by using the override signal to override the motor control signal.

In some embodiments, the difference signal in the method described above preferably further comprises an amplified difference between a desired pressure input and the pressure sensor input. In some embodiments, the step of providing the difference signal in the method described above preferably comprises providing proportional control of a pulse width modulation duty cycle. In some embodiments, the step of generating the motor control signal in the method described above preferably comprises generating a pulse width modulation signal. In some embodiments, the step of preventing the pump motor from stalling in the method described above preferably comprises logically ANDing the override signal with the motor control signal. In some embodiments, the method described above preferably further comprises the step of preventing the pump motor from initially running at a substantially 100% duty cycle.

In some embodiments, a method for treating a wound is provided, preferably comprising the steps of providing a wound dressing, a fluid collection container, a vacuum pump, one or more tubes, and a pressure sensor configured to measure a pressure in one or more of said one or more tubes, and controlling a pump motor to provide a negative pressure to the wound dressing without using a processor. In some embodiments, the one or more tubes are preferably configured to at least channel a flow of fluid between the wound dressing, the fluid collection canister, and the pump. In some embodiments, the step of controlling a pump motor to provide a negative pressure to the wound dressing preferably comprises the steps of receiving a pressure sensor input from the pressure sensor, outputting a motor control signal responsive to the pressure sensor input and a desired pressure input, and outputting an override signal based at least in part on the pressure sensor input and the desired pressure input.

In some embodiments, the pressure sensor input in the method described above preferably reflects the pressure in one or more of said one or more tubes. In some embodiments, the motor control signal is preferably configured to control a speed of the pump motor. In some embodiments, the override signal is preferably configured to override the motor control signal in order to prevent the pump motor from stalling. In some embodiments, the method described above further comprises the step of activating a low pressure alarm in response to the pressure sensor input having a value less than about half of the desired pressure input.

In some embodiments, an apparatus for detecting high air flow in a negative pressure wound therapy system for the treatment of wounds is provided, preferably comprising a wound dressing, a fluid collection container, a vacuum pump, one or more tubes configured to at least channel a flow of fluid between said wound dressing, said fluid collection canister, and said pump, a first pressure sensor configured to measure a pressure in one or more of said one or more tubes at a first location and to generate a first output signal, a second pressure sensor configured to measure a pressure in said tubing at a second location apart from said first location and to generate a second output signal, a difference circuit configured to provide a difference signal reflecting a difference between the first and second output signals, a comparison circuit configured to provide a comparison signal based at least in part on the difference signal and a threshold signal, and an alarm circuit configured to produce an alarm responsive to the comparison signal, the alarm reflecting a high flow condition. In some embodiments, the apparatus described above preferably further comprises an integrator circuit interposed between the difference circuit and the comparison circuit, the integrator circuit preferably being configured to introduce a delay between the difference circuit and the comparison circuit.

BRIEF DESCRIPTION OF THE DRAWINGS

These and other features, aspects and advantages will now be described in connection with certain embodiments, in reference to the accompanying drawings. The illustrated embodiments, however, are merely examples and are not intended to be limiting. The following are brief descriptions of the drawings.

DETAILED DESCRIPTION OF SOME EXEMPLIFYING EMBODIMENTS

Figure 1:
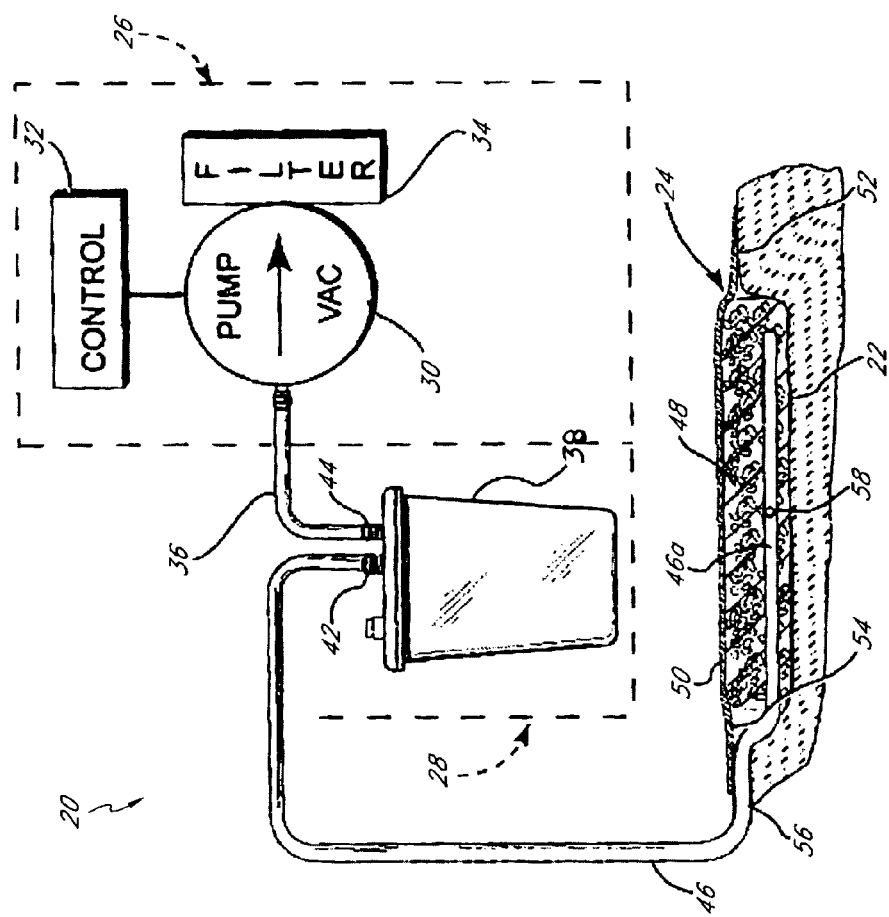
FIG. 1 is a schematic view of an embodiment of negative pressure wound therapy apparatus.

The following detailed description is now directed to certain specific embodiments of the disclosure. In this description, reference is made to the drawings wherein like parts are designated with like numerals throughout the description and the drawings.

Preferred embodiments described herein relate to wound therapy. The term "wound" as used herein, in addition to having its broad ordinary meaning, includes any body part of a patient that may be treated using reduced pressure. Wounds include, but are not limited to, open wounds, pressure sores, ulcers and burns. Treatment of such wounds can be performed using negative pressure wound therapy, wherein a reduced or negative pressure can be applied to the wound to facilitate and promote healing of the wound. Additional descriptions of devices, methods and systems that may be used for wound therapy are found in U.S. Patent Application Publication No.

2004/0073151 A1 and U.S. Pat. No. 7,128,735, the entirety of both of which are hereby incorporated by reference and made a part of the present disclosure. It will also be appreciated that the negative pressure systems and methods as described herein may be applied to other parts of the body, and are not necessarily limited to treatment of wounds.

Certain embodiments are directed to a pressure control circuit for use with a medical device or system for conducting negative pressure wound therapy. A pressure control circuit embodied in such a medical device can be subject to FDA approval. Typical motor controllers used in medical devices use a processor, such as a microcontroller or the like, for controlling a motor. Software or firmware is written for the processor that includes instructions for controlling the motor. However, the inventors have discovered several disadvantages of using microcontrollers. For example, using software in a medical device for which FDA approval is sought presents a disadvantage because software and firmware are often subject to a more stringent FDA approval process than hardware circuits. This approval process can include the submission of time-consuming and expensive documentation on testing and risk factors. Thus, using a processor for pressure control can be undesirable.

Moreover, processors can include many components such as transistors. The vast number of transistors used in some processors, including even the simplest microcontrollers, present a risk of failure. If even one of the transistors fails, in many instances the entire control circuit fails, possibly resulting in adverse consequences to a medical patient. Thus, safety concerns motivate not using processors for pressure control. In addition, it can be more cost-effective to use components that are less expensive than a processor.

Accordingly, the inventors have developed embodiments of a pressure control circuit and other vacuum pump circuitry that do not include a processor. The pressure control circuit instead includes analog and/or digital (non-processor) circuitry that reduces or completely eliminates some or all of the problems described above. FIGS. 1 through 4 illustrate certain aspects of negative pressure wound therapy systems that can embody the pressure control circuit. FIGS. 5 through 9 illustrate certain aspects of pressure control circuitry and other vacuum pump circuitry.

FIG. 1 is a schematic view of an embodiment of a negative pressure wound therapy apparatus 20. As described herein, the negative pressure wound therapy apparatus is preferably configured to treat a wound by application of reduced pressure to a wound site 22 (e.g., below atmospheric pressure) so as to provide suction to the wound site 22 in a controlled manner for a selected period of time.

As illustrated in FIG. 1, the negative pressure wound therapy apparatus 20 comprises a wound cover or wound dressing 24 for enclosing a wound site 22 and providing a fluid-tight or gas-tight enclosure over the wound site 22 to effect treatment of a wound site 22 with reduced or negative pressure. For the purpose of creating suction within the wound dressing 24, the wound dressing 24 is connected to a vacuum system 26 to provide a source of suction or reduced pressure for the sealed wound dressing 24 at the wound site 22. Between the wound dressing 24 and the vacuum system 26 is a fluid collection system 28 for intercepting and retaining exudate that is aspirated from the wound site 22.

It should be noted that any wound cover or dressing presently known in the art or developed in the future can be configured to be integrated into the negative pressure wound therapy apparatus 20 described herein. For example, the embodiments of the wound covering device set forth in U.S. Pat. No. 7,128,735, which disclosure is hereby incorporated by reference herein in its entirety, can be used in place of the flexible wound dressing 24 illustrated in FIG. 1. One available type of wound enclosure is the Chariker-Jeter wound sealing kit from BlueSky Medical, Inc.

As shown in FIG. 1, the vacuum system 26, which produces a source of reduced pressure or suction that is supplied to the wound dressing 24, preferably comprises a vacuum pump 30, a vacuum system control device 32, a filter 34, and tubing 36 that connects the vacuum pump 30 to the collection system 28. Predetermined amounts of suction or reduced pressure are produced by the vacuum pump 30. The vacuum pump 30 is preferably controlled by a control device 32 that will be described in greater detail below (see, e.g., FIGS. 5-9). A filter 34, such as micropore filter, is attached to the exhaust of the vacuum pump 30 to prevent potentially pathogenic microbes or aerosols from the wound site 22 from being vented to the atmosphere by the vacuum pump 30. In some embodiments, not shown, the filter may preferably be positioned between the fluid collection system 28 and pump 30 along tubing 36 such that the pump may be protected from contaminated fluids. In some embodiments, the vacuum system 26 of the negative pressure wound therapy apparatus 20 can comprise two or more vacuum pumps 30 connected with tubing 36, preferably arranged in parallel. The additional pump 30 may ensure a higher level of safety and product quality by providing pump redundancy to prevent vacuum system failure in the event that a single pump fails, in addition to more efficiently providing increased suction.

The fluid collection system 28 is preferably interconnected between the suction vacuum pump 30 and the appliance 24 to remove and collect any exudate which may be aspirated from the wound site 22 by the wound dressing 24. The appliance 24 preferably functions to actively draw fluid or exudate from the wound site 22. Collection of exudate in a fluid collection system 28 between the vacuum pump 30 and the appliance 24 is preferred to prevent clogging of the vacuum pump 30.

As illustrated in FIGS. 1-2, 3D, and 3E, the fluid collection system 28 may be comprised of a fluid-impermeable collection container 38 and a shutoff mechanism 40. The container 38 may be of any size and shape suitable for intercepting and retaining a predetermined amount of exudate. Many examples of such containers are available in the relevant art. The container 38 illustrated preferably has a first port 42 and a second port 44 positioned on the top of the container 38. The first port 42 preferably enables suction to be applied to the wound dressing 24 through the tubing 46 and also enables exudate from the wound site 22 covered by wound dressing 24 to be drained into the container 38. The container 38 provides a means for containing and temporarily storing the collected exudate. A second port 44 is also provided on the top of the container 38 to enable the application of suction from the vacuum pump 30 to the container 38. As mentioned above, the second port 44 of the collection system 28 is connected to the vacuum pump 30 by a vacuum line 36. The collection system 28 is preferably sealed approximately gas-tight so that as to enable the suction vacuum pump 30 to supply suction to the appliance 24 through the collection system 28.

The fluid-impermeable wound cover 50 in the embodiment of the wound dressing 24 illustrated in FIG. 1 may be in the form of a flexible, adhesive, fluid impermeable polymer sheet for covering and enclosing the wound site 22, including an optional absorbable matrix 48 within it, and the surrounding normal skin 50 around the wound site 22. In further embodiments the matrix may be non-bioabsorbable, as is known in the art. The wound cover 50 preferably includes an adhesive backing 54 which functions to seal the wound cover 50 to the normal skin 52 around the periphery of the wound site 22 so as to provide a generally gas-tight or fluid-tight enclosure over the wound site 22. The adhesive cover 40 preferably has sufficient adhesion to form a fluid-tight or gas-tight seal around the periphery of the wound site 22 and to hold the cover 50 in sealed contact with the skin 52 during the application of suction or reduced or negative pressure. The wound cover 50 also preferably provides a gas-tight seal around the tubing 46 at the feedthrough location 56 where the tubing 46 emerges from beneath the wound cover 50. The tube segment 46a embedded within the absorbable matrix 48 preferably has at least one side port 58 positioned within the interior of the absorbable matrix 48 to enable a substantially uniform application of reduced pressure throughout the enclosure.

The absorbable matrix 48 can be placed over substantially the expanse of the wound site 22 to encourage growth of tissue in the area of the wound site 22 into the matrix 48 as the wound heals. The size and configuration of the absorbable matrix 48 can be adjusted to fit the individual wound site 22. It can be formed from a variety of absorbable materials, preferably a material that is also porous. The matrix 48 should be constructed in a manner so that it is sufficiently porous to allow oxygen to reach the wound site 22. The absorbable matrix 48 is preferably constructed of a non-toxic material that is absorbable by the epithelial and subcutaneous tissue within the area of the wound site 22, such as collagens derived from healthy mammals, absorbable synthetic polymers, or other materials similar to those used for absorbable dressings. However, other materials for and configurations of the absorbable matrix 48 can be used with the negative pressure wound therapy apparatus 20 disclosed herein, such as is described in U.S. Patent Application Publication No. US 2004/0073151 A1, which is incorporated by reference herein in its entirety.

Figure 2:
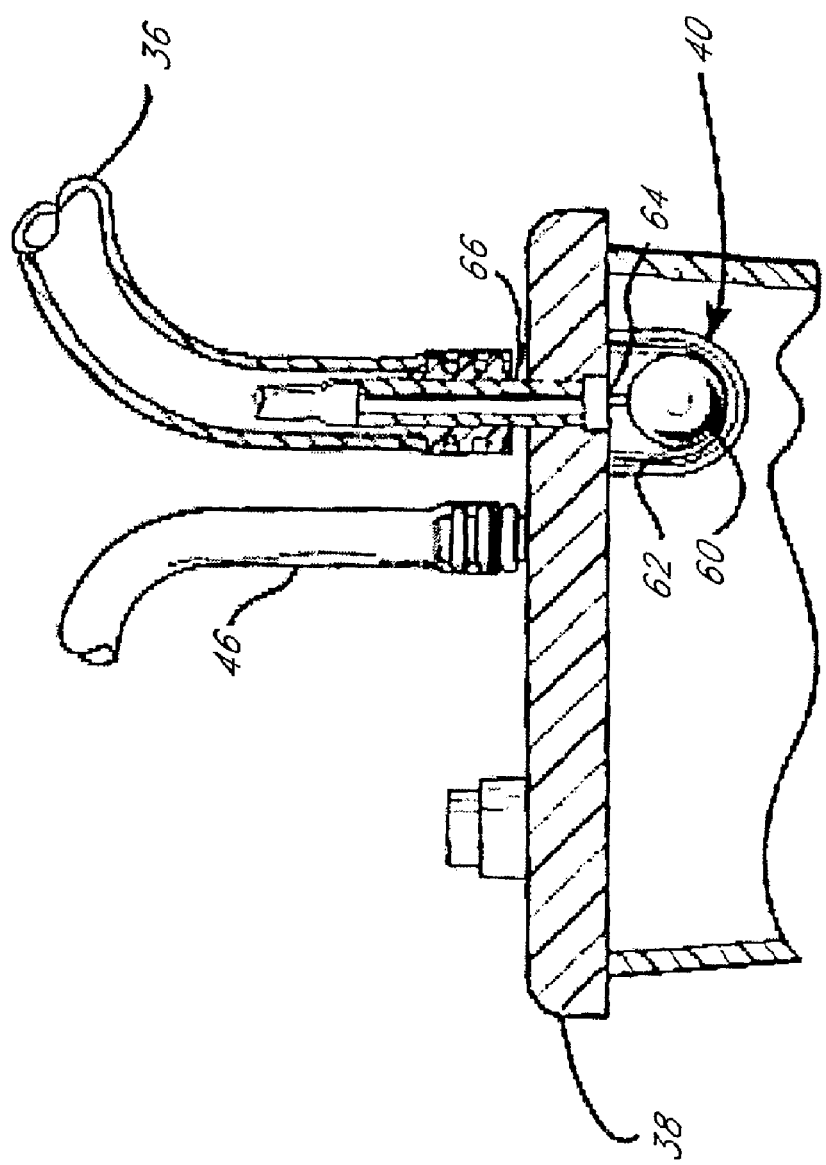
FIG. 2 is a section view of a portion of an embodiment of a collection system.

FIG. 2 is a section view of the collection system 28 of the negative pressure wound therapy apparatus 20 illustrated in FIG. 1. As previously stated, the vacuum system 26 and collection system 28 preferably include a shutoff mechanism 40 for halting or inhibiting the supply of the reduced pressure to the appliance 24 in the event that the exudate aspirated from the wound 22 exceeds a predetermined quantity. Interrupting the application of suction to the appliance 24 is desirable to prevent exsanguination in the unlikely event a blood vessel ruptures under the wound cover 50 during treatment. If, for example, a blood vessel ruptures in the vicinity of the wound 22, a shutoff mechanism may be useful to prevent the vacuum system 26 from aspirating any significant quantity of blood from the patient.

The shutoff mechanism 40 may be comprised of any means that enables the vacuum system 26 to halt the supply of reduced pressure to the wound cover 50 at any time that the volume of exudate from the wound 22 exceeds a predetermined amount. Such means may include mechanical switches, electrical switches operably connected to the vacuum system control device 32, optical, thermal or weight sensors operably connected to the vacuum system control device 32, and any other means that are currently known in the relevant art or are suitable for this function.

The shutoff mechanism 40, as illustrated in FIG. 2, is preferably a float valve assembly comprising a ball 60 which is held and suspended within a cage 62 positioned below a valve seat 64 disposed within the opening at the top of the container below the second port that will float upon the exudate and will be lifted against the valve seat 64 as the container fills with exudate. When the ball 60 is firmly seated against the valve seat 64, the float valve blocks the second port 66 and thereby shuts off the source of suction from the vacuum system 26. Other types of mechanisms may also be employed to detect the liquid level within the container 38 in order to arrest operation of the vacuum system 50.

Figure 3A:
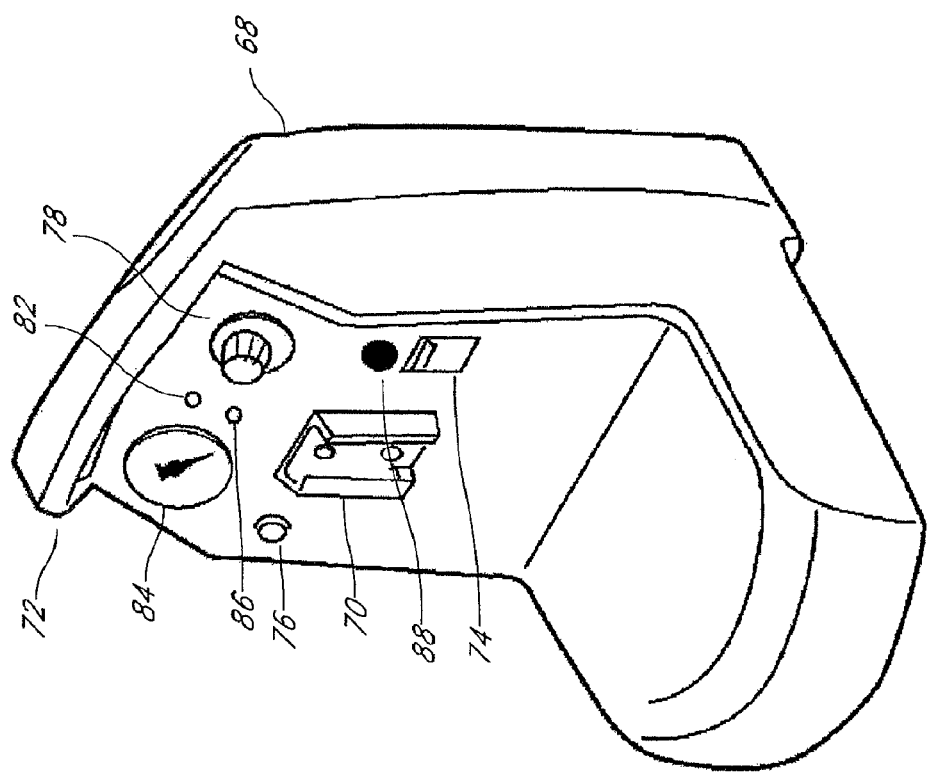
FIG. 3A is a perspective view of the outside of an embodiment of an enclosure for a negative pressure wound therapy apparatus.
Figure 3C:
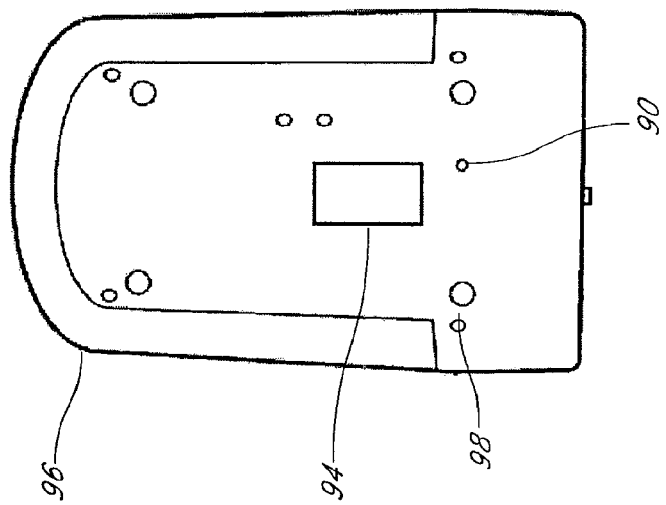
FIG. 3C is a planar view of the bottom side of an embodiment of the enclosure illustrated in FIG. 3A.
Figure 3B:
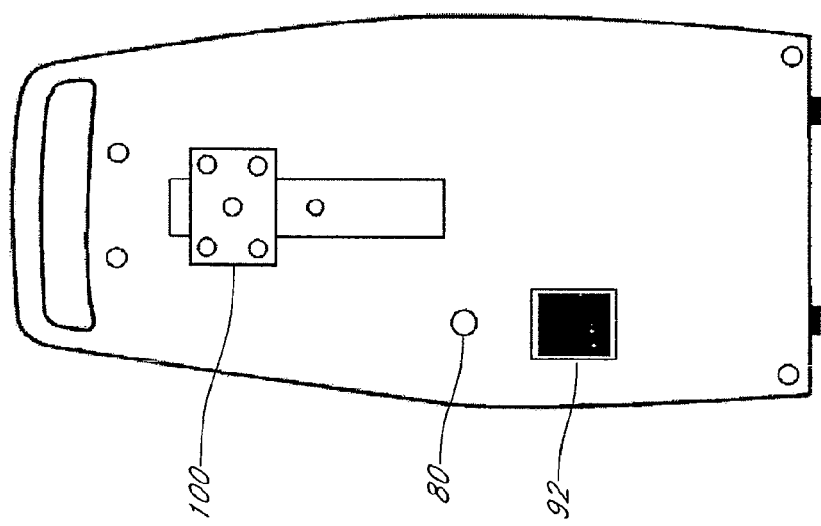
FIG. 3B is a planar view of the back side of an embodiment of the enclosure illustrated in FIG. 3A.

FIG. 3A is a perspective view of an embodiment of the outside of a enclosure 68 for a negative pressure wound therapy apparatus, FIG. 3B is a planar view of the back side of the enclosure illustrated in FIG. 3A, and FIG. 3C is a planar view of the bottom side of the enclosure illustrated in FIG. 3A. The enclosure 68 illustrated in FIGS. 3A-3C can be used to enclose and/or support many of the components and features comprising some embodiments of the negative pressure wound therapy apparatus described herein. In the illustrated embodiment, the enclosure 68 preferably encloses and/or supports the fluid collection system and vacuum system, including but not limited to the vacuum pump, vacuum system control device, filter, and tubing that connects the vacuum pump to the collection system.

Additionally, as illustrated in FIGS. 3A-3C, the enclosure 68 preferably also supports or comprises a container adapter bracket 70, a handle 72, a power switch 74, a vacuum port 76, a pressure selector 78 which switches the pump configuration from a continuous to an intermittent output configuration, a 12 volt DC input 80, a low pressure LED light 82, a pressure/vacuum gauge 84, a low battery LED light 86, an alarm suppress button 88, an air exhaust outlet 90, an AC power inlet and fuse 92, a specification badge 94, a rolling stand connection 96, rubber feet 98, and a universal holder bracket 100.

The low pressure LED light 82 is preferably configured to warn the user of the negative pressure wound therapy apparatus when the vacuum level is low or there is a leak in the system. Pressing the alarm suppress button 88 will suppress the low pressure LED light 82 after it has been activated. The low battery LED light 86 is preferably configured to warn the user of the negative pressure wound therapy apparatus when the battery power level is low. The low battery LED light 86 may be accompanied by an audible warning noise or "chirp" when the battery power level is low. Pressing the alarm suppress button 88 will suppress the low battery LED light 86 and/or audible warning noise. The enclosure 68 also preferably includes a lithium ion rechargeable battery (not shown) that is recharged when an AC power supply is connected to the enclosure 68.

Figure 3E:
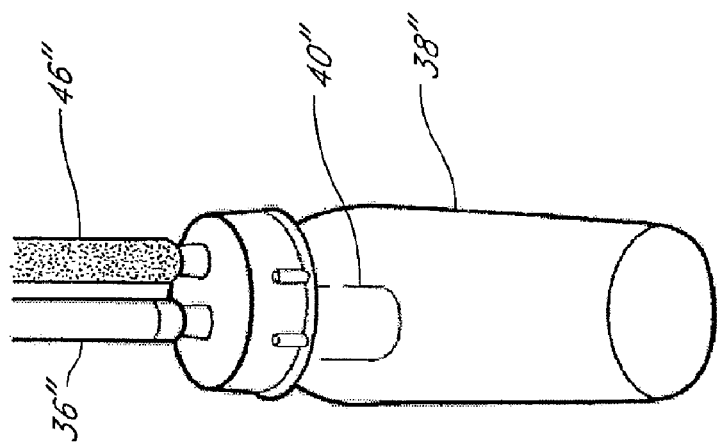
FIG. 3E is a perspective view of the outside of another embodiment of a fluid collection container.
Figure 3D:
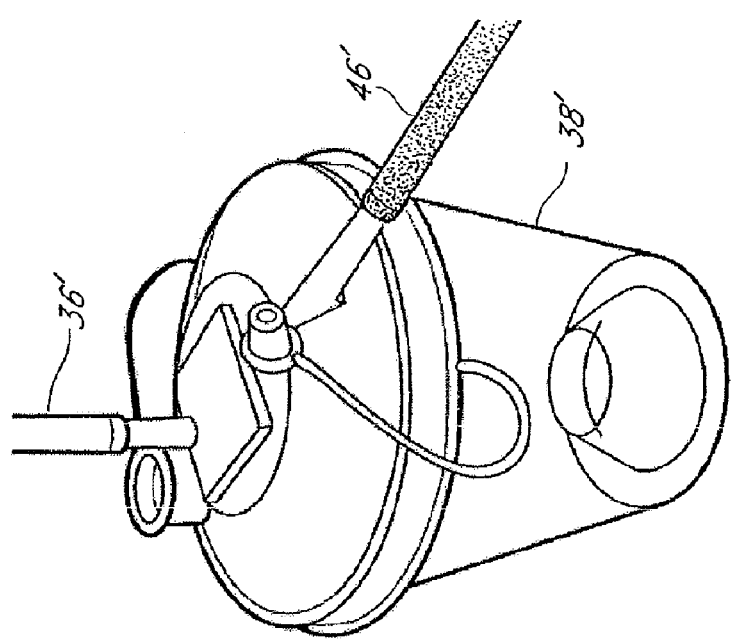
FIG. 3D is a perspective view of the outside of an embodiment of a fluid collection container.

FIG. 3D is a perspective view of the outside of another embodiment of a fluid collection container 38' that can be secured to the container adapter bracket 70 of the enclosure 68 described above. In the illustrated embodiment, the volume of the fluid collection container 38' is approximately 800 cubic centimeters. The fluid collection container 38' is preferably connected to the vacuum pump 30 by tubing 36', and to the wound dressing 24 through the tubing 46'. Additionally, the fluid collection container 38' illustrated in FIG. 3D preferably comprises a shutoff mechanism (not shown) to halt or inhibit the supply of the reduced or negative pressure to the appliance 24 in the event that the exudate aspirated from the wound 22 exceeds a predetermined quantity.

FIG. 3E is a perspective view of the outside of another embodiment of a fluid collection container 38" that can be secured to the container adapter bracket 70 of the enclosure 68 described above. In the illustrated embodiment, the volume of the fluid collection container 38" is approximately 250 cubic centimeters. The fluid collection container 38" is preferably connected to the vacuum pump 30 by tubing 36", and to the wound dressing 24 through the tubing 46". Additionally, the fluid collection container 38" illustrated in FIG. 3E preferably comprises a shutoff mechanism 40" to halt or inhibit the supply of the reduced or negative pressure to the appliance 24 in the event that the exudate aspirated from the wound 22 exceeds a predetermined quantity.

Figure 4:
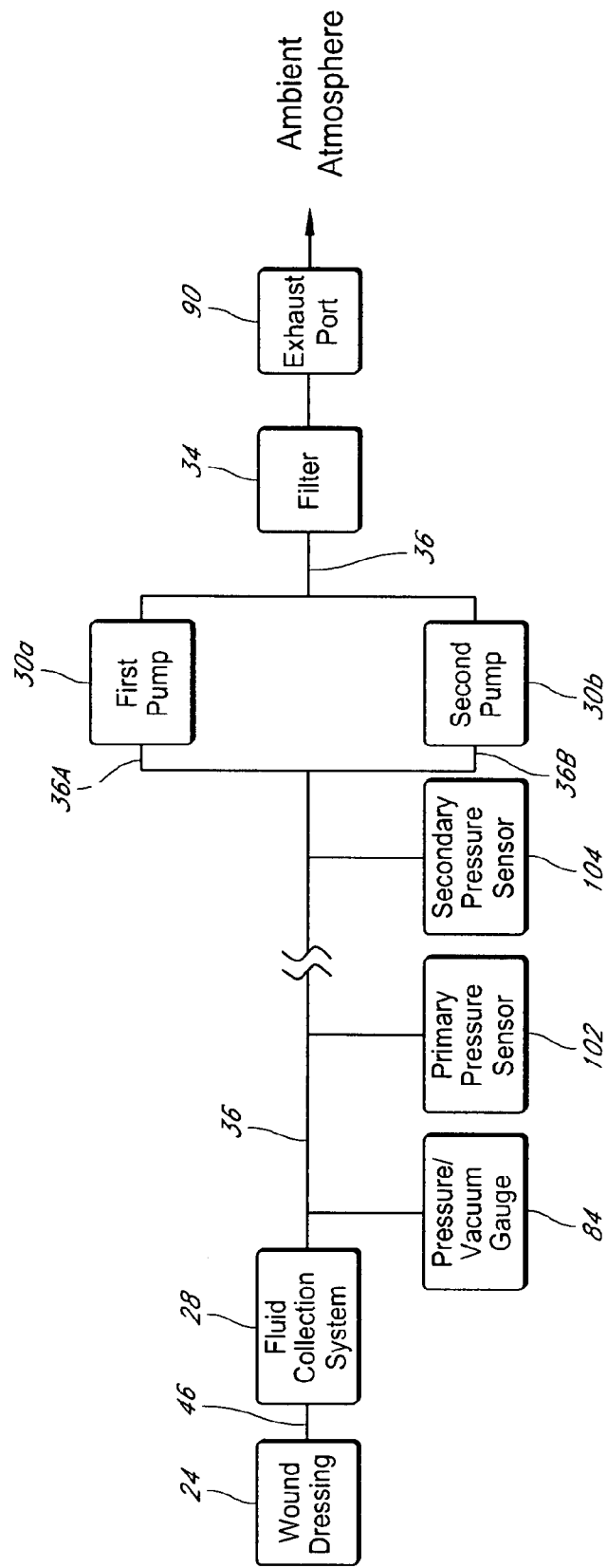
FIG. 4 is a schematic representation of an embodiment of the vacuum system.

FIG. 4 is a schematic representation of an embodiment of the vacuum system 26, illustrating the suction and exhaust circuits and the relative position of the components therein. In the illustrated embodiment, a first pump 30a and a second pump 30b are connected in parallel via tubing 36A, 36B, respectively, which are joined to tubing 36 using a standard tubing connector. The addition of the second pump 30b may ensure a higher level of safety and product quality by providing pump redundancy to prevent vacuum system failure in the event that a single pump fails, in addition to more efficiently providing increased suction. Tubing 36A, 36B then joins the outlet flow from the first and second pumps 30a, 30b together using a standard tubing connector, and channels the outlet flow through the filter 34 and then out through the exhaust port 90 to the ambient atmosphere.

In the illustrated embodiment, the vacuum system 26 preferably has a primary pressure sensor 102 and a secondary pressure sensor 104. As illustrated in FIG. 4, the primary pressure sensor 102 is located further upstream from the pumps 30a, 30b as compared to the secondary pressure sensor 104 (i.e., of the two pressure sensors 102, 104, the primary pressure sensor 102 is preferably located closer to the wound dressing 24 in the illustrated embodiment). Describing the components according to their preferred position in the illustrated embodiment relative to the pumps 30a, 30b, the secondary pressure sensor 104 is preferably positioned to read the pressure in the tubing 36 upstream of the pumps 30a, 30b. The secondary pressure sensor 104 detects the fluid pressure within the tubing 36 and is preferably configured to shut down the power to both pumps 30a, 30b when the pressure reading by the secondary pressure sensor 104 exceeds a predetermined threshold value. The pressure reading by the secondary pressure sensor 104 may exceed a predetermined threshold value when, for example, the shutoff mechanism 40 is activated. While just a single pressure sensor could be used to operate the negative pressure wound therapy apparatus 20, an additional pressure sensor allows for flow rate measurements to help detect leaks in the system and to activate a high flow rate alarm, among other reasons, as discussed below.

Positioned to read the pressure further upstream, e.g., in the direction of the fluid collection container 38 and the wound dressing 24, the primary pressure sensor 102 detects the pressure in the tubing between the secondary pressure sensor 104 and the fluid collection container 28. The primary pressure sensor 102 preferably provides instantaneous or near-instantaneous pressure values to the vacuum system control device 32 that is preferably used to control the vacuum pump 30. The primary pressure sensor 102 can also be configured to activate the circuitry of the low pressure alarm, e.g., the low pressure LED light 82, when the pressure detected by the primary pressure sensor 102 is lower than a predetermined value for a significant amount of time.

The primary pressure sensor 102 and/or the secondary pressure sensor 104 can be of any suitable configuration known in the art, such as, but not limited to, an ASDX series pressure transducer manufactured by Honeywell Sensing and Control. In some embodiments, the primary pressure sensor 102 and/or the secondary pressure sensor 104 are preferably located on the control board used to control an output of one or more pumps 30.

In some embodiments, the low pressure alarm is activated when the pressure detected by the primary pressure sensor 102 is lower than a predetermined value for approximately forty seconds or longer, or for approximately fifty seconds or longer, or for approximately sixty seconds or longer, or for approximately seventy seconds or longer, or for approximately eighty seconds or longer, or for approximately one hundred seconds or longer, or for approximately one hundred twenty seconds or longer, or for approximately one hundred thirty seconds or longer.

In some embodiments, pressure sensors 102, 104 can be slightly apart from each other or can be adjacent to each other. However, in other embodiments, such as the illustrated embodiment, the sensors 102, 104 can be a greater distance apart from each other. In addition, a flow restrictor (not shown) or the like can be positioned between the sensors 102, 104 to restrict air flow in the tubing 36 between the sensors 102, 104. The flow restrictor can be, for example, a small mechanical orifice, a thin, relatively long tube, combinations of the same, or the like. By restricting the flow between the two pressure sensors 102, 104, the flow restrictor may better enable the pressure sensors 102, 104 to obtain differential pressure measurements. The pressure differential measurements can be used to calculate the flow rate of air in the tubing 36, as the pressure difference can be proportional to the flow rate. Moreover, in embodiments where thin tubing is used, the length of the tubing can determine the amount of air resistance and hence the amount of pressure difference generated in the tubing. A high flow rate can indicate the presence of a leak in the tubing, wound bed, or the like. If a leak occurs, an alarm can be triggered to alert a clinician. Example circuits for determining air flow, detecting leaks, and/or triggering alarms is shown and described below with respect to FIGS. 8 and 9.

During normal operation, the flow of air through the tubing 36 is sufficiently small such that there may be only a negligible pressure difference between the two pressure sensors 102, 104. However, if there are substantial leaks in the system, the pumps 30a, 30b will run at a higher level of output and air will flow more quickly through the tubing 36, causing the pressure differential between the two sensors 102, 104 to increase to a more easily detectable range. The pressure values collected from the primary pressure sensor 102 and the secondary pressure sensors 102 will preferably provide a pressure differential. In some embodiments, a high flow alarm will be activated when the pressure differential between the two pressure sensors 102, 104 is approximately 5 mmHg or greater. In some embodiments, a high flow alarm will be activated when the pressure differential between the two pressure sensors 102, 104 is approximately 7.5 mmHg or greater. In some embodiments, a high flow alarm will be activated when the pressure differential between the two pressure sensors 102, 104 is approximately 10 mmHg or greater. Additional embodiments using pressure sensors to detect high flow are shown and described below with respect to FIGS. 8 and 9.

Additionally, in some embodiments, the vacuum system control device 32 is preferably configured to comprise an intermittent delay function. In some embodiments, the intermittent delay preferably reduces the overall duty cycle of the pumps 30a, 30b by approximately 20% or more. In some embodiments, the intermittent delay preferably reduces the overall duty cycle of the both pumps 30a, 30b by approximately 30% or more. In some embodiments, the intermittent delay preferably reduces the overall duty cycle of the both pumps 30a, 30b by approximately 40% or more. In some embodiments, the intermittent delay preferably reduces the overall duty cycle of the both pumps 30a, 30b by approximately 50% or more. In this manner, the intermittent delay preferably controls the output of the pumps 30a, 30b so as to cycle the pressure between a range of values. An example intermittent delay circuit is shown and described below with respect to FIG. 9.

Figure 5:
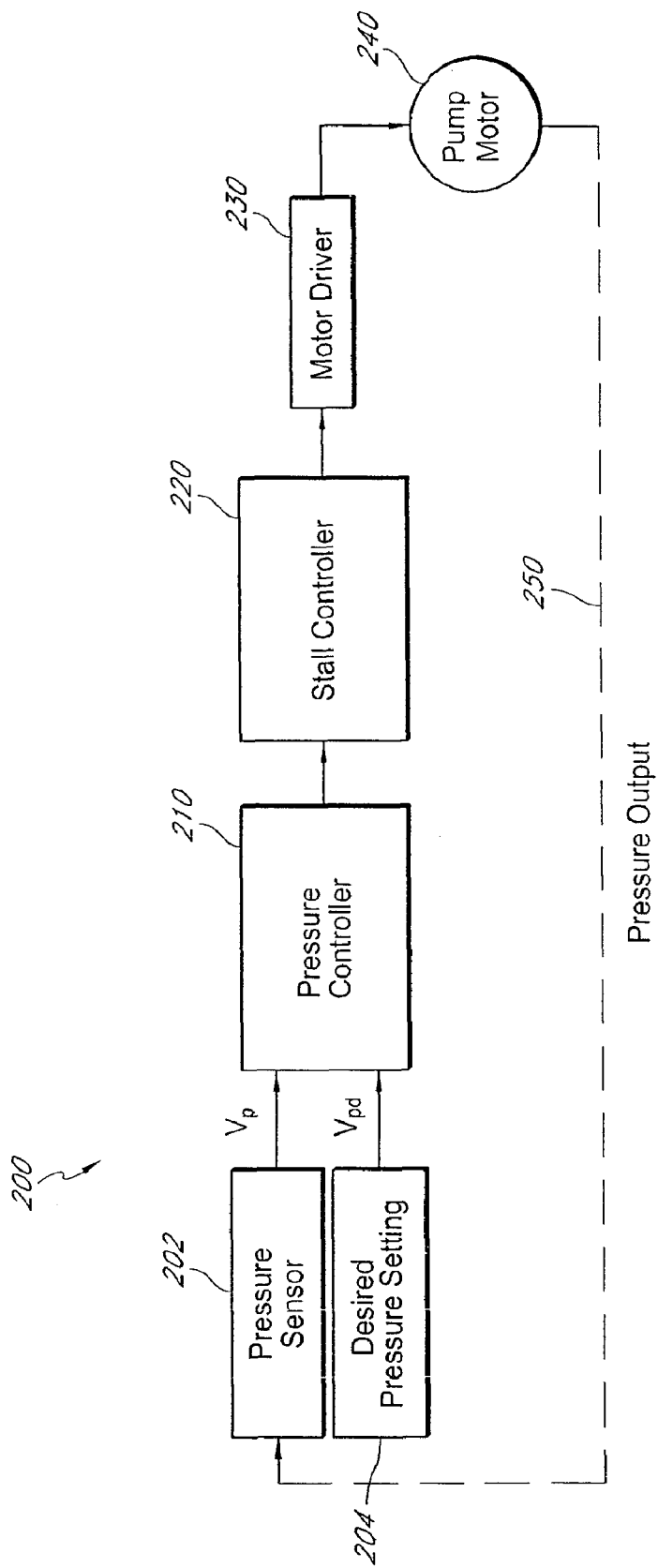
FIG. 5 is a block diagram of an embodiment of a pressure control circuit.

FIG. 5 illustrates an embodiment of a pressure control circuit 200. The pressure control circuit 200 controls the pressure in the plumbing of one or more vacuum pumps, such as any of the vacuum pumps described above. Certain embodiments of the pressure control circuit 200 advantageously control the pressure of the pump plumbing without using a microcontroller.

In the pressure control circuit 200, a pressure sensor 202 or the like is provided as a transducer for converting sensed pressure in the pump plumbing into a pressure voltage $V_p$. The pressure sensor 202 can include, for example, a piezoelectric material that alters its electrical characteristics as pressure at the piezoelectric material changes. The pressure of the pump system, and hence the pressure voltage $V_p$, can change over time. Thus, the pressure voltage $V_p$ can be a time-varying voltage signal.

A desired pressure voltage $V_{pd}$ is also provided to the pressure controller 210 by a desired pressure setting 204. The desired pressure setting 204 can be a hardwired pressure setting (e.g., using a resistor network or the like) or a user-defined pressure setting. The desired pressure setting 204 can be provided, for example, by an input device such as a knob or button that can be adjusted by a user. In one embodiment, described below, the desired pressure setting 204 is provided using an encoder that converts a value on a knob or dial into the desired pressure voltage $V_{pd}$.

The pressure voltage $V_p$ and desired pressure voltage $V_{pd}$ can be provided to a pressure controller 210. In certain embodiments, the pressure controller 210 includes one or more circuit components for adjusting the pressure provided by a pump motor 240 such that the pressure voltage is the same or substantially the same as the desired pressure voltage. Advantageously, the pressure controller 210 of certain embodiments includes analog circuit components rather than a processor such as a microcontroller. In some implementations, some non-processor digital circuitry can also be provided.

The pressure controller 210 uses the pressure voltage $V_p$ and the desired pressure voltage signal $V_{pd}$ to control the pressure in the pump plumbing. The pressure controller 210 can control the pressure by causing or by attempting to cause the pressure sensed by the pressure sensor 202 to be equal to or substantially equal to the desired pressure setting 204. The pressure controller 210 therefore attempts to keep the pressure voltage $V_p$ close to the desired pressure voltage $V_{pd}$.

The pressure controller 210 of certain embodiments changes pressure in the pump plumbing by adjusting the power, voltage, or current provided to the pump motor 240. By adjusting one or more of these parameters (e.g., power), the pressure controller 210 can increase or decrease the speed of the pump motor 240. As the pump motor 240 increases or decreases speed, the pressure output 250 generated by the pump motor 240 increases or decreases respectively. Thus, by controlling the power or the like sent to the pump motor 240, the pressure controller 210 can control the pressure in the pump plumbing.

As an example, if the pressure voltage $V_p$ is less than the desired pressure voltage $V_{pd}$, the pressure controller 210 can increase the speed of the pump motor 240. As the pump motor increases speed 240, the pressure sensed by the pressure sensor 202 increases, and hence the pressure voltage $V_p$ increases. If, on the other hand, the pressure voltage $V_p$ is more than the desired pressure voltage $V_{pd}$, the pressure controller 210 can decrease the speed of the pump motor 240, thereby causing pressure to fall and the pressure voltage $V_p$ to decrease. In certain embodiments, the pressure controller 210 continually increases and decreases the speed of the pump motor 240 to compensate for decreases and increases in pressure voltage $V_p$, respectively. However, certain override circuits, such as an intermittent delay circuit described below with respect to FIG. 9, can halt the continuous adjustments made by the pressure controller 210.

The pressure controller 210 could be used as the sole pump motor 240 controller in some implementations. However, the pump motor 240 can stall when not enough power is provided to the pump motor 240 to make the coils of the pump motor 240 turn. In stall conditions, the power provided to the pump motor 240 can be wasted. Stalling can occur, for example, when the pressure voltage $V_p$ is higher than the desired pressure voltage $V_{pd}$. To compensate for the higher pressure voltage $V_p$, the pressure controller 210 might reduce the power provided to the pump motor 240. If the pressure controller 210 causes too little power to be provided, the pump motor 240 will stall.

To prevent stalling from occurring, a stall controller 220 is provided that receives one or more output signals from the pressure controller 210. The stall controller 220 of certain embodiments cuts power to the pump motor 240 in the event of an impending stall condition. The stall controller 220 can do this by, for example, overriding the pressure controller 210. Advantageously, the stall controller 220 can prevent stall conditions without using a processor. Instead, the stall controller 220 of various embodiments includes analog and/or digital (non-processor) circuitry that efficiently prevents the pump motor 240 from stalling.

For example, the stall controller 220 can include logic such as an AND gate or the like. The stall controller 220 can generate an override signal that is gated at the AND gate with an output signal from the pressure controller 210. In an embodiment, the override signal is active-low. Thus, if the override signal is at a high voltage or logic state, the override signal enables the output from the pressure controller 210 to effectively pass through the AND gate. If, however, the override signal is at a low voltage or logic state, the override signal can override the output from the pressure controller 210, effectively preventing this output from reaching the pump motor 240. It should be understood that while the override signal has been described as an active-low signal, the override signal can also be active-high in some implementations. Likewise, other active-low signals described herein can be active-high in some embodiments, and vice versa.

In certain embodiments, the output of the stall controller 220 is a combined control signal, which is provided to a motor driver 230. The motor driver 230 facilitates providing power to the pump motor 240. In an embodiment, the motor driver 230 includes one or more transistors (e.g., MOSFETs), relays, or the like that act as a power switch responsive to the combined control signal. A more detailed example of a motor driver 230 is shown and described below with respect to FIG. 9.

Figure 6:
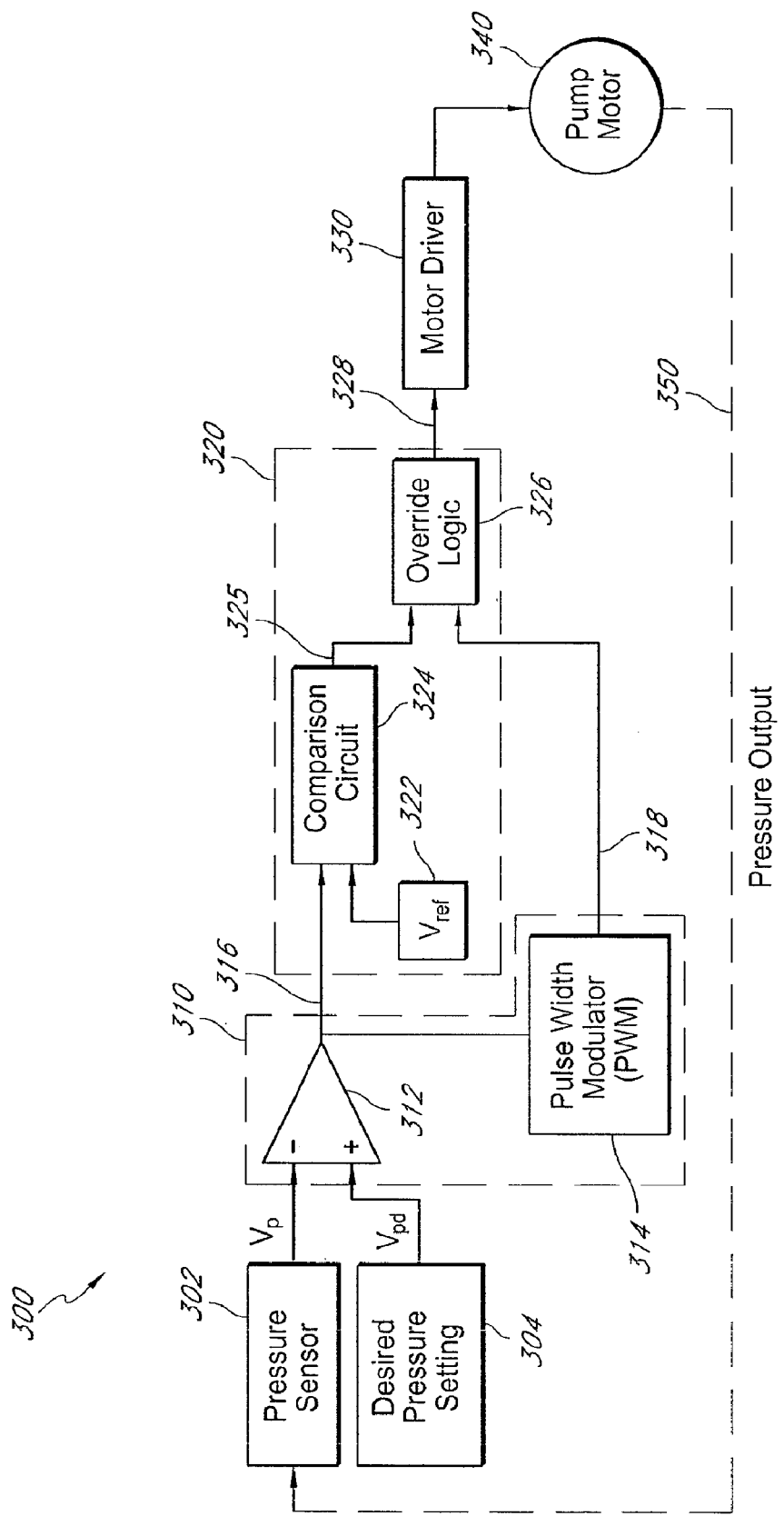
FIG. 6 is a schematic block diagram of another embodiment of a pressure control circuit.

FIG. 6 illustrates a more detailed embodiment of a pressure control circuit 300. The depicted embodiment of the pressure control circuit 300 includes several of the components of the pressure control circuit 200. For example, a pressure sensor 302, a desired pressure setting 304, a motor driver 330, and a pump motor 340 are provided. In certain embodiments, these components have the same functions as those described above with respect to FIG. 5. In addition, more detailed views of a pressure control circuit 310 and a stall control circuit 320 are provided.

The pressure control circuit 310 of certain embodiments includes a difference circuit 312 in communication with a pulse width modulator 314. In one embodiment, the difference circuit 312 includes an amplifier, such as a differential amplifier. The difference circuit 312 receives a pressure voltage $V_p$ from the pressure sensor 302 and a desired pressure voltage $V_{pd}$ from the desired pressure setting 304. The difference circuit 312 can determine a difference in voltage between the pressure voltage $V_p$ and the desired pressure voltage $V_{pd}$ to output a difference signal 316. This difference signal 316 can also be referred to as an error signal because the difference signal 316 can represent the error between the desired pressure voltage $V_{pd}$ and the actual pressure voltage $V_p$. In addition, the difference circuit 312 can amplify the difference between the two voltages. The amplification value can be unity in certain implementations.

In various embodiments, the difference circuit 312 includes an operational amplifier or "op amp." A network of passive circuit elements, such as resistors, capacitors, and/or the like, can be provided on the inputs, outputs, and in a feedback loop of the difference circuit 312. These passive circuit elements can be used to adjust the amplification value or gain of the amplifier and/or the frequency characteristics of the amplifier. A more detailed embodiment of the difference circuit 312 having a network of passive circuit elements is described below with respect to FIG. 9.

In one embodiment, the difference circuit 312 has a gain value of about 6; however, this gain value can take on many other values in other embodiments. In addition, the difference signal 316 in some embodiments is not a pure difference between the pressure voltage $V_p$ and the desired pressure voltage $V_{pd}$. Instead, the difference circuit 312 can be configured with supporting passive circuits elements such that the difference signal 316 is represented as:

$$A*(V_p - V_{pd}) + V_{pd}, \quad (1)$$

where A in expression (1) is an amplification or gain value.

The difference signal 316 is provided to the pulse width modulator 314 and to the stall controller 320. The pulse width modulator 314 of certain embodiments includes a comparator, op amp, or the like having supporting passive circuit components for generating a variable duty cycle square wave. This square wave is provided by the pulse width modulator 314 as a motor control signal 318 to the stall controller 320. A more detailed example of a comparator circuit for implementing the pulse width modulator 314 is shown and described below with respect to FIG. 9.

The square wave of the motor control signal 318 is selectively provided, through the stall controller 320, to the motor driver 330. When the motor control signal 318 is in a logic high state, the motor control signal 318 causes the motor driver 330 to provide power to the pump motor 340. Conversely, when the motor control signal 318 is in a logic low state, the motor control signal 318 prevents the motor driver 330 from providing power to the pump motor 340. The motor control signal 318 can accomplish this by actuating a transistor (e.g., MOSFET) or relay power switch. Thus, as the duty cycle of the motor control signal 318 increases, power is provided more frequently to the pump motor 340, causing the speed of the pump motor 340 to increase, and vice versa. Advantageously, using pulse width modulation enables speed control of the pump motor 340 without loss of torque.

The square wave of the motor control signal 318 can have a duty cycle ranging from 0% to 100%. The duty cycle is controlled in certain embodiments by the difference signal 316. As the difference signal 316 increases, the duty cycle can increase, and vice versa. Thus, as the difference (or error) signal 316 increases in magnitude, the duty cycle can increase, and as the difference signal 316 decreases, the duty cycle can decrease. In an embodiment, the pressure controller 310 therefore acts as a proportional controller, changing the speed of the motor in proportion to the amount of error. In other embodiments, integral and/or derivative control can be provided in addition to proportional control, such as to create a proportional-integral-derivative (PID) controller.

Both the difference signal 316 and the motor control signal 318 can be provided to the stall controller 320. In certain implementations, the stall controller 320 includes a comparison circuit 324 and override logic 326. In addition, the stall controller 320 can include or receive a voltage reference 322. The stall controller 320 advantageously prevents the pump motor 340 from stalling, thereby increasing the efficiency of the pressure control system 300.

The comparison circuit 324 includes a comparator, an op amp in comparator configuration, or the like. The comparison circuit 324 compares the difference signal 316 to the voltage reference 322 to produce an override signal 325. In one embodiment, if the difference signal 316 is greater than the voltage reference 322, the comparison circuit 324 outputs a logic high (or high voltage) value. On the other hand, if the difference signal 316 is less than the voltage reference 322, the comparison circuit 324 outputs a logic low (or low voltage) value. Thus, the override signal 325 is high or low depending on whether the difference signal 316 is higher or lower than the voltage reference 322, which is a predetermined threshold voltage value. In certain embodiments, the override signal 325 can be considered active low, meaning that the override signal 325 overrides the motor control signal 318 when the override signal 325 is low.

Accordingly, if the difference (error) signal 316 is greater than the voltage reference 322, the comparison circuit 324 effectively determines that the error is sufficiently high to allow the pressure controller 310 to control the pump motor 340. However, if the difference (error) signal 316 is lower than the voltage reference 322, then the comparison circuit 324 effectively determines that the error is too low, such that the pressure controller 310 might stall the pump motor 340. In this low error situation, the comparison circuit 324 can use the override signal 325 to override the pressure control circuit 310, thereby preventing stalling of the pump motor 340.

While the pump motor 340 is off, the pressure in the pump tubing will drop. As a result, the error or difference signal 316 will increase. Eventually, the difference signal 316 will increase enough to cause the comparison circuit 324 to deactivate the override signal 325, so that the stall controller 320 will allow the pressure controller 310 to take over control of the pump motors 340 again.

While a single voltage reference 322 is shown, an additional voltage reference is provided to enable the comparison circuit 324 to provide hysteresis. In an embodiment, the two voltage references are offset from one another by an optionally small voltage amount. For example, depending on the type, manufacturer, and/or part number of the pressure sensor 302 or other components used, one voltage reference could be set at 1.0 volts and the other voltage reference could be set at 1.2 volts. Other voltage values could be chosen in various embodiments, as is described in more detail below with respect to FIG. 9. If the difference signal 316 is above the higher voltage reference, the comparison circuit 324 outputs a logic high value. If the difference signal 316 is below the lower voltage reference, the comparison circuit 324 outputs a logic low value. If the difference signal 316 is between the two voltage references, the comparison circuit 324 does not change the override signal 325 value. Hysteresis can prevent the comparison circuit 324 from switching rapidly in response to minor changes in the difference signal 316.

The override signal 325 is provided, in certain embodiments, to the override logic 326. The override logic 326 includes one or more analog or digital circuit components that facilitating selectively overriding the motor control signal 318. For instance, the override logic 326 can include an AND gate or the like. As described above, the override signal 325 can be gated at the AND gate with the motor control signal 318, facilitating the selective overriding of the motor control signal 318. The override logic 326 outputs a combined control signal 328 that is provided to the motor driver 330. The combined control signal 328 can reflect the combined control of the pressure controller 310 and the stall controller 320. Thus, if the override signal 325 is high (or not active) in one embodiment, then the combined control signal 328 is effectively the motor control signal 318. However, if the override signal 325 is low (or active), then the combined control signal 328 has a low (not active) output, which does not drive the motor driver 330 and therefore prevents the pump motor 340 from stalling.

While the override circuit 324 has been described with respect to an AND gate, other circuit components can be used. For example, one or more OR, NAND, NOR, XOR, combinations of the same, or other gates can be configured to provide an AND function. In addition, discrete or integrated transistor components can be used to accomplish an AND function. Moreover, in other embodiments, analog circuit components can be used to accomplish an equivalent AND function. Other logic functions, such as the OR, NAND, NOR, XOR, or other functions, could also be used in place of the AND function.

In certain implementations, the stall controller 320 uses the override signal 325 to effectively keep the duty cycle of the pulse width modulator 314 within a certain range during a steady state of the pump motor 340. An ideal duty cycle in one embodiment is 40%. In another embodiment, a desired duty cycle range is 40% to 45%. In still other embodiments, the desired range is 35% to 45%.

Viewed another way, in certain embodiments the pressure control circuit 310 provides linear control and the stall control circuit 320 provides nonlinear control. If the duty cycle of the pulse width modulator 314 is above a target duty cycle value, e.g., 40%, the pressure control system 300 may be operating in linear control mode, using the pressure control circuit 310. If the duty cycle falls below this range, however, the pressure control system 300 may operate in nonlinear mode, using the stall controller 320.

Figure 7A:
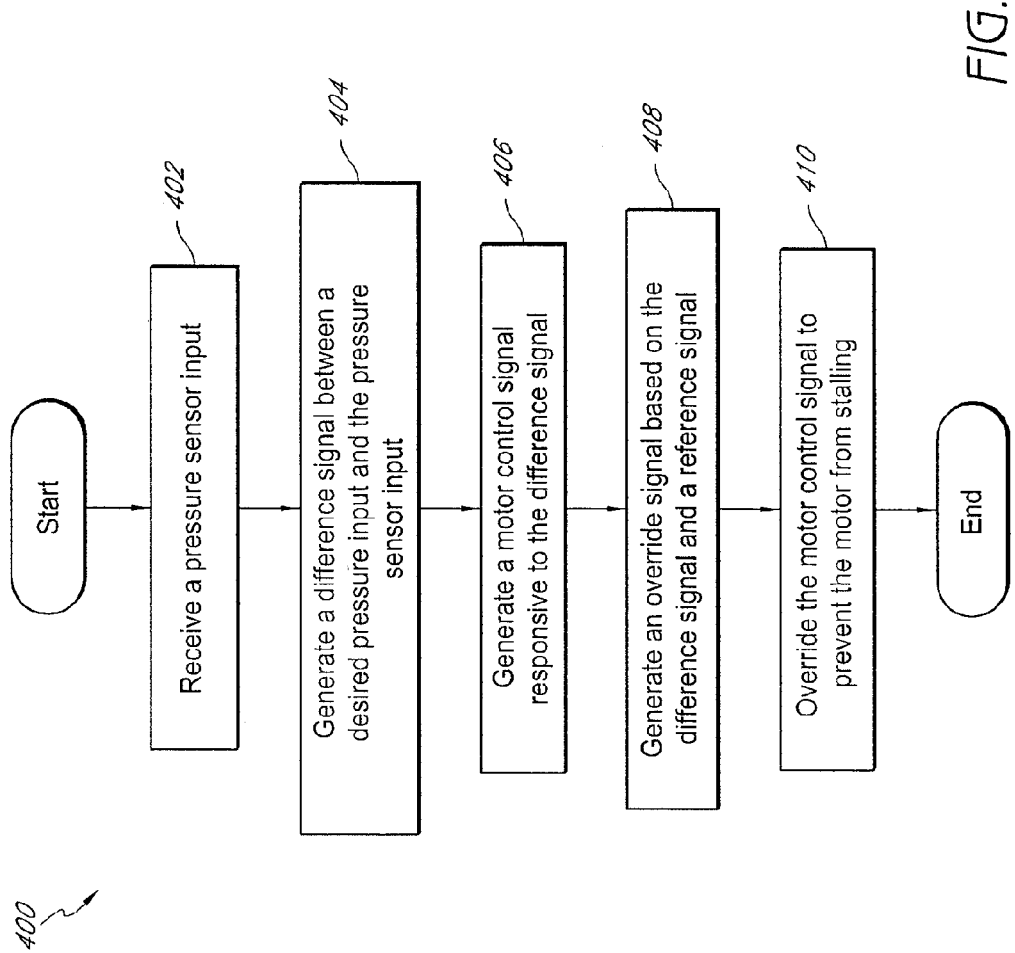
FIG. 7A is an embodiment of a process for controlling a pump motor.

FIG. 7A illustrates an embodiment of a process 400 for controlling a pump motor. The process 400 can be implemented in certain embodiments by any of the pressure control systems described above. Advantageously, the process 400 can therefore be implemented without using a processor. Moreover, the process 400 can be used in conjunction with negative wound pressure therapy techniques, such as those described above.

The process 400 begins at block 402 by receiving a pressure sensor input. The pressure sensor input can be a voltage or current signal from a pressure sensor. In an embodiment, this input is provided by a pressure sensor, such as any of the pressure sensors described above. At block 404, the process 400 generates a difference signal between a desired pressure input and the pressure sensor input. The desired pressure input can be provided by, for example, a user through an input device. The difference signal can represent an error between desired and actual pressure inputs. This difference signal can be used to control the speed of a pump motor.

Continuing, at block 406 the process 400 generates a motor control signal responsive to the difference signal. The motor control signal can be a pulse-width modulated signal or have other signal characteristics. At block 408, the process 400 generates an override signal based at least in part on the difference signal and on at least one reference signal. One or more reference signals can be provided to compare with the difference signal. If the difference signal is above or below a reference signal, for instance, the process 400 can perform certain actions. For example, at block 410, the process 400 can override the motor control signal to prevent the motor from stalling.

In certain embodiments, the process 400 overrides the motor control signal in response to the difference signal being lower than at least one reference signal. As the pressure increase due to the turning off of the pump motor, the difference signal will increase until the difference signal is above the reference signal. At this point, the override signal will deactivate, allowing the motor control signal to control the speed of the pump motor.

Advantageously, the process 400 provides for motor control without stalling a motor. In particular, the process 400 increases the efficiency of power usage by the motor by avoiding stalling conditions.

Figure 7B:
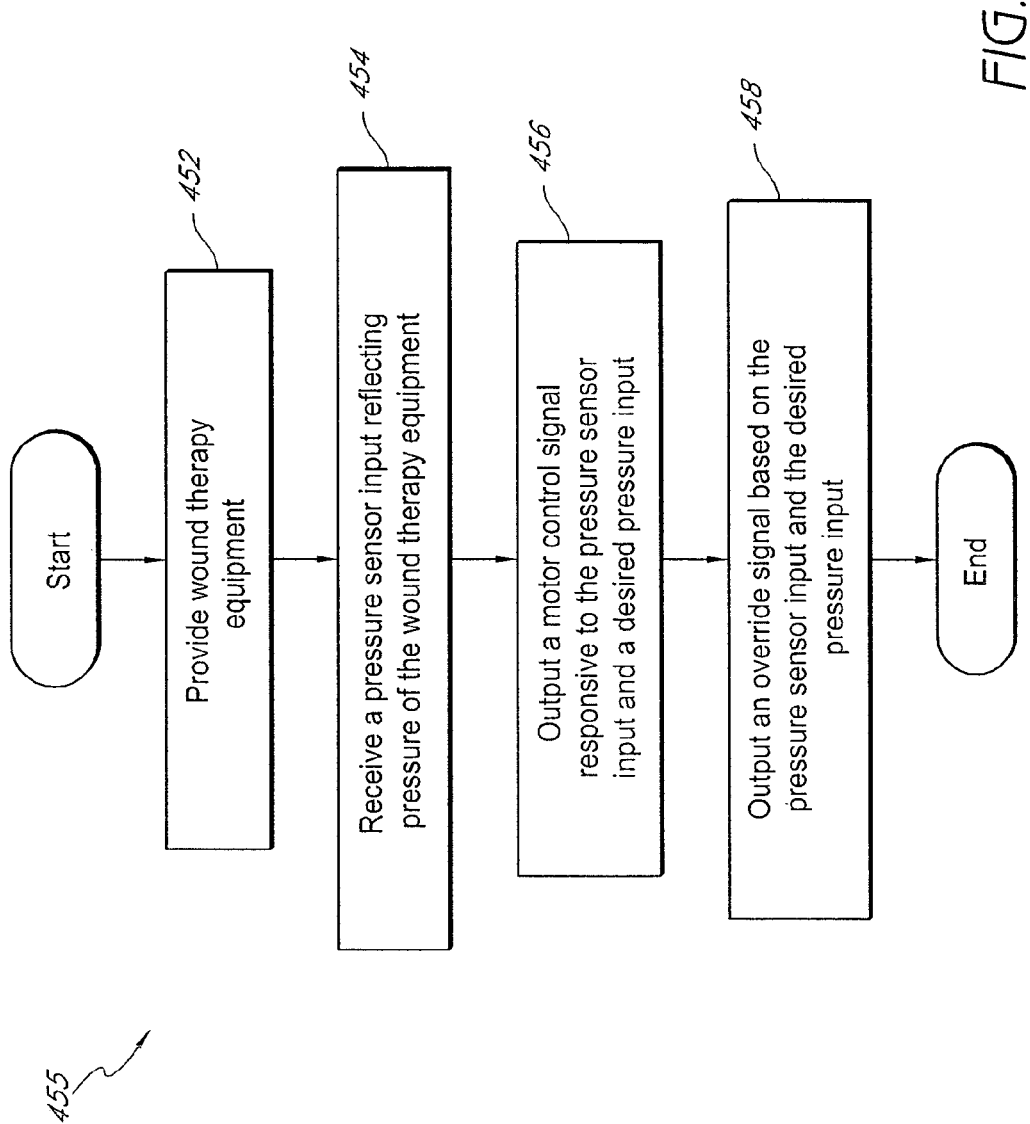
FIG. 7B is an embodiment of a process for treating a wound.

FIG. 7B illustrates an embodiment of a process 450 for treating a wound. The process 450 can be implemented in certain embodiments by any of the negative pressure wound therapy systems described above, including any of the pressure control systems described above. Advantageously, the process 450 can therefore be implemented without using a processor.

At block 452, the process begins by providing wound therapy equipment. This equipment can include, for example, a wound dressing, a fluid collection container, a vacuum pump, and a pressure sensor. The pressure sensor can measure a pressure in the tubing of the vacuum pump, the wound bed, or the like. In certain embodiments, one or more tubes in the tubing of the vacuum pump channel a flow of fluid between the wound dressing, the fluid collection canister, and the pump.

Continuing, at block 454 the process 450 receives a pressure sensor input from the pressure sensor. This pressure sensor input can reflect the pressure of the wound therapy equipment. The pressure can be the pressure inside the tubing, at the wound bed, or the like. At block 456, the process 450 outputs a motor control signal responsive to the pressure sensor input and a desired pressure input. The motor control signal is operative to control the speed of one or more pump motors. The desired pressure input can be provided, for example, by a user through an input device such as a knob, button, or the like.

The process 450 also outputs an override signal at 450. This override signal can be based at least in part on the pressure sensor input and the desired pressure input. For example, the override signal could be based on a difference between these inputs. In certain embodiments, this difference is an error signal. As described above, as the error is reduced, the override signal can be provided to prevent the motor from stalling.

Advantageously, the process 450 enables a medical patient's wound to be treated more effectively and safely than can be done with currently available vacuum pump devices.

Figure 8:
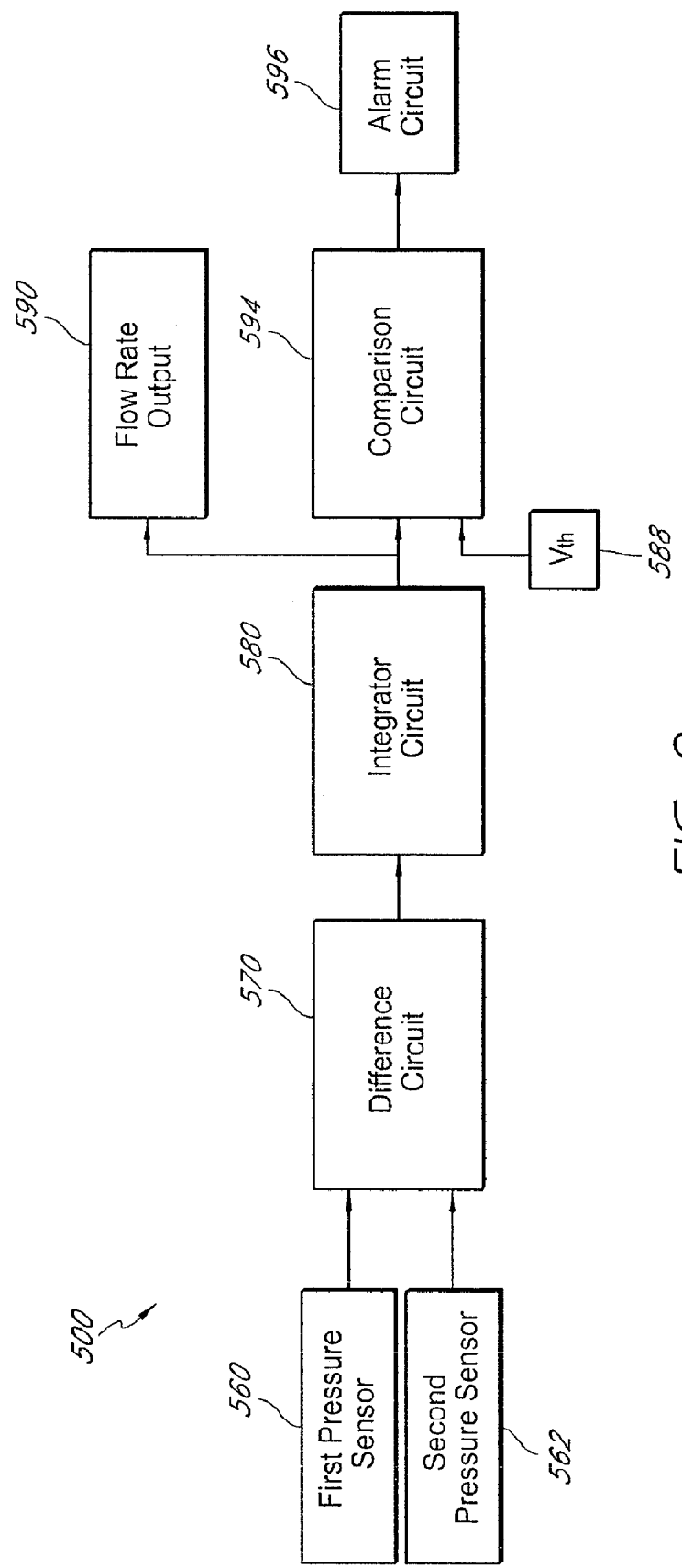
FIG. 8 is a block diagram of an embodiment of a high flow detection and alarm circuit.

FIG. 8 illustrates an embodiment of a high flow detection circuit 500. The high flow detection circuit 500 of certain embodiments can detect potential leaks in a vacuum pump system used for negative pressure wound therapy. The high flow detection circuit 500 can, in various embodiments, provide a measurement of the flow of air and/or an alarm that alerts clinicians to the leak condition.

In various embodiments, the high flow detection circuit 500 includes first and second pressure sensors 560, 562. One or more of the pressure sensors 560, 562 can be similar to the pressure sensor described above. Moreover, in certain embodiments, one or more of the pressure sensors 560, 562 can also be used as a pressure sensor in a pressure control system, such as any of the pressure control systems described above.

The pressure sensors 560, 562 can be connected by a flow restrictor or the like as described above to facilitate determining air flow. In a non-leak condition, in one embodiment little or no air is moving through the tubing. Thus, each of the pressure sensors 560, 562 can measure the same or substantially the same pressure level. However, if a leak occurs, air moving through the flow restrictor can create a pressure difference between the sensors 560, 562.

In an embodiment, a difference circuit 570 is provided for measuring this pressure difference. The difference circuit 570 can be an amplifier, such as an operational amplifier or the like. In addition, the difference circuit 570 can be a comparator. Many other implementations may be chosen, an example of which is shown and described with respect to FIG. 9. The difference circuit 570 outputs a difference signal.

The difference circuit 570 provides the difference signal to the integrator circuit 580. In one embodiment, however, the difference circuit 570 first provides the difference signal to a low pass filter (not shown) for reducing noise in the difference signal, which in turn provides the difference signal to the integrator circuit 580. In certain embodiments, the integrator circuit 580 is also a low pass filter or the like that integrates the difference signal using, for example, one or more capacitors and resistors. By integrating the difference signal, the integrator circuit 580 provides a delay that can prevent the comparison circuit 590 from rapidly switching an alarm on and off.

The integrator circuit 580 in one embodiment provides a flow rate signal as a flow rate output 590. In certain embodiments, the flow rate is proportional to the pressure differential between the two signals, as measured by the difference signal. The flow rate output 590 can be provided to a gauge, digital display, or the like. The flow rate output 590 can also be provided earlier in the high flow detection circuit 590, for example, after the difference circuit or after a low pass circuit (not shown). In addition to, or in place of providing the flow rate signal to the flow rate output 590, the integrator circuit 580 can provide the flow rate signal to a comparison circuit 594. In certain embodiments, the comparison circuit 594 compares the flow rate signal to a threshold voltage 588, $V_{th}$. If the flow rate signal exceeds the threshold voltage 588, in certain embodiments a leak is detected.

The comparison circuit 594 can in turn provide an alarm signal to an alarm circuit 596 in the event of detecting a leak. The alarm circuit can alert a clinician using, for example, audible and/or visual alarms. Thus, the clinician can take corrective action to repair the leak.

Figures 1, 2, 9:
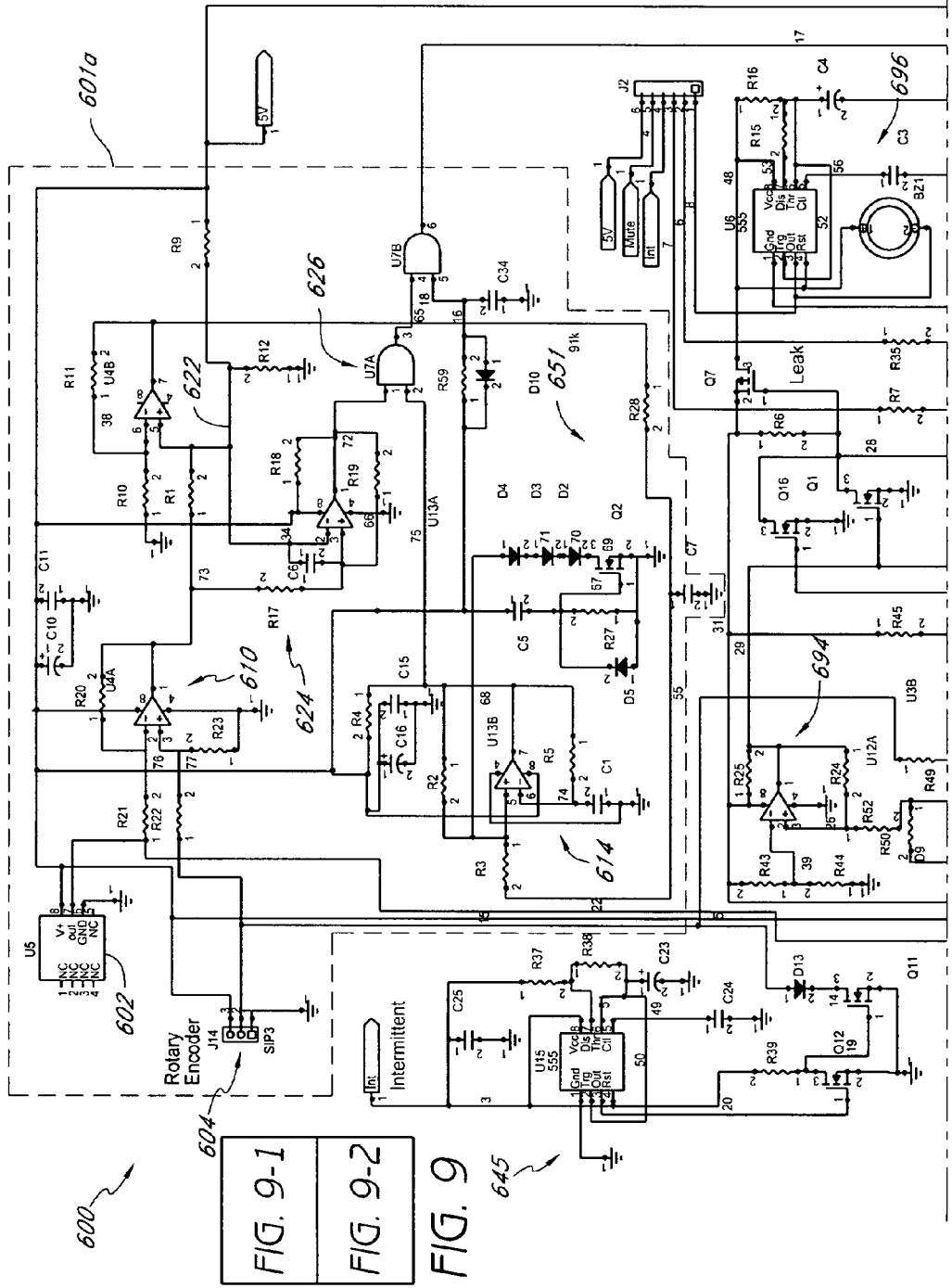
FIG. 9 is a block diagram of an embodiment of a negative wound pressure therapy system.
Figures 2, 9:
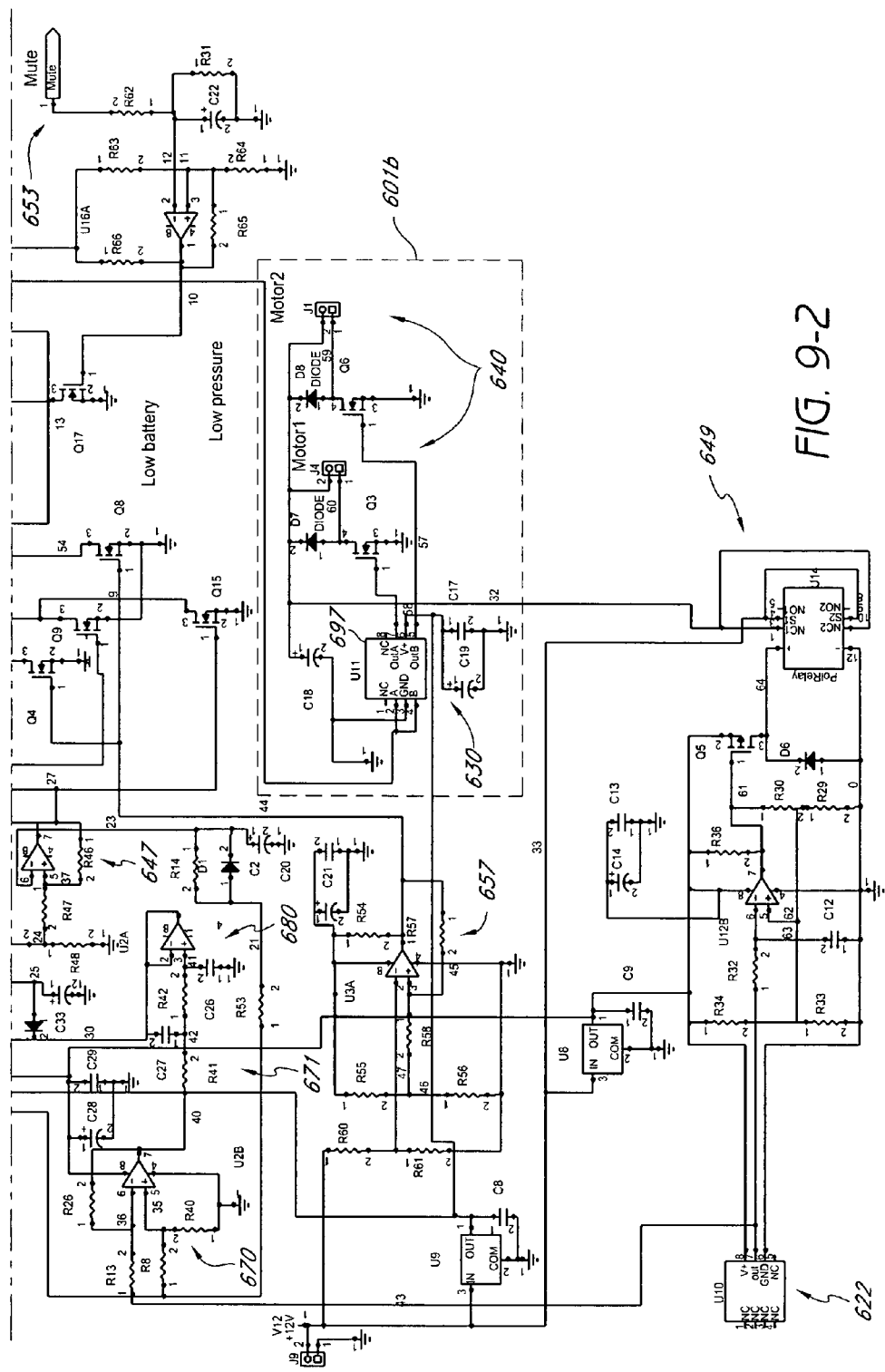

FIG. 9 illustrates an embodiment of a vacuum pump circuit 600. The vacuum pump circuit 600 includes a pressure control circuit 601 along with several other exemplary circuits useful for vacuum wound pressure therapy. In the depicted embodiment, no processor is used, thereby facilitating one or more of the benefits described above. In addition, two pump motors 640 are provided, facilitating further fault protection and increased suction.

Some or all of the voltage values described herein can vary based on the type, manufacturer, and/or part number of the pressure sensors used. Additionally, the voltage values can vary based on the particular type, manufacturer, and/or part numbers of the resistors, capacitors, diodes, transistors, integrated circuit components, combinations of the same, or the like that are used. Thus, other voltage values than those described herein can result from the choice of various sensors and/or components in various embodiments, without departing from the scope of the embodiments described herein.

The pressure control circuit 601 as shown includes pressure control circuits 601a and 601b. The pressure control circuit 601a includes a pressure sensor 602 and a desired pressure setting provided by an encoder input 604. Like the pressure sensors and desired pressure settings described above, the pressure sensor 602 and the encoder input 604 provide voltage signals to a pressure control circuit having an amplifier 610 (the op amp U4A) and a pulse width modulator 614. In the depicted embodiment, the pulse width modulator 614 includes a comparator U13B, a capacitor C1, and resistors, which together generate a variable duty cycle square wave.

The amplifier 610 and the pulse width modulator 614 both provide outputs to a stall control circuit, which includes a voltage reference 622, a comparison circuit 624, and override logic 626. In the depicted embodiment, the voltage reference 622 is generated by using a resistive divider using resistors R9 and R12 to lower a 5 volt input to about 1.2 volts. The comparison circuit 624 includes a comparator U13A and associated resistors. The override logic includes an AND gate U7A.

In an embodiment, the comparison circuit 624 generates a high logic or voltage value in response to an input signal greater than about 1.26 volts and generates a low logic or voltage value in response to an input signal lower than about 1.06 volts. Between about 1.06 and 1.26 volts, the comparison circuit 624 does not change its output. Thus, the comparison circuit 624 of certain embodiments employs hysteresis, as discussed above.

In certain embodiments, the operation of the pressure control circuit 601 is as follows. The pressure in the vacuum tubing at startup of the circuit is zero or substantially zero, which is much lower than the encoder input 604. Therefore, a difference signal between the pressure sensor input 602 and the encoder input 604 is greater than 1.26V, causing the comparison circuit 624 to output high, allowing the output of the pulse width modulator 614 to reach the pump motors 640.

The duty cycle of the pulse width modulator 614 can be determined by the magnitude of the difference signal, starting at about 100% and decreasing to about 40% as the pressure nears the encoder input 604. The pressure continues to increase and eventually rises past the encoder input 604 by a few millimeters (mmHg), causing the difference signal to fall below 1.06V. This in turn causes the comparison circuit 624 output to go low, cutting power to the pump motors 640. The pressure then slowly falls below the encoder input 604 by a few mmHg, causing the difference signal to rise above 1.26V, in turn causing the comparison circuit 624 to output high. This high output once again allows the pulse width modulator 614 to apply power the pump motors 640. This cycle can continue indefinitely (e.g., until the pump is turned off by a user or the like), maintaining the pressure at the encoder input 604 value within a few mmHg by occasionally pulsing the pump motors 640 with short bursts of about 20 kHz square wave at about 40% duty cycle. Example pressure values of when the pump motors 640 can turn on and off are shown below in Table 1.

TABLE 1

Comparison Circuit Output

| | Encoder input (mmHg) | | | | | | | | | | |
|---|---|---|---|---|---|---|---|---|---|---|---|
| | 200 | 180 | 160 | 140 | 120 | 100 | 90 | 80 | 70 | 60 | 50 | 40 |
| Pumps ON (mmHg) | 199 | 179 | 159 | 139 | 120 | 100 | 90 | 80 | 70 | 60 | 50 | 40 |
| Pumps OFF (mmHg) | 201 | 182 | 162 | 142 | 122 | 102 | 92 | 82 | 72 | 62 | 52 | 42 |

The pulse width modulator 614 of certain embodiments does not have a fixed operating frequency. Instead, its frequency can vary with duty cycle, in a fixed, bell shaped relationship. Frequency can peak near 50% at about 25 kHz, dropping to about 8 kHz at 9% and 90% duty cycle.

In certain embodiments, the output to a motor driver circuit 630 is logically ANDed at AND gate U7B with a pump soft-start circuit 651, which is shown as part of the pressure control circuit 601. The motor driver circuit 630 can include an integrated circuit 697 including one or more transistor (e.g., power MOSFET) drivers, discrete transistor drivers, supporting passive component circuitry, combinations of the same, or the like. In alternative embodiments, the pump soft-start circuit 651 is not included with the pressure control circuit 601. The pump soft-start circuit 651 helps ensure that the pump motors 640 do not draw too much current at power on to avoid the protection circuitry in the power supply shutting down the power supply. This circuit is described in further detail below.

In addition to the pressure control circuit 601, a depicted flow rate detection circuit is provided that includes first and second pressure sensors 602, 662, a difference circuit 670, an integrator circuit 680, a comparison circuit 694, and an alarm circuit 696. In an embodiment, the pressure sensor 602 used for pump control is also used for flow rate detection. In addition, a second, backup sensor 662 is also used. In one embodiment, these sensors 602, 662 are both connected to the same general area of the pump plumbing, but spaced slightly apart so that they will measure slightly different pressures as air flows through the plumbing. During normal operation, flow can be so small that there is almost no pressure difference between the sensors. If the suction load were removed, the pumps can run full speed and the flow of air through the plumbing could be much larger.

The difference between the sensors 602, 662 is amplified by a gain of 20 at the difference circuit 670, low pass filtered by a low pass filter 671, and then fed to the integrator circuit 680, which has a 66 second time constant. The integrator circuit 680 output goes to a comparison circuit 694 with a fixed threshold of 1.56 volts in the depicted embodiment. The output of the comparison circuit 694 is provided to the alarm circuit 696, which drives various transistors (e.g., MOSFETs) to turn on a piezoelectric beeper or the like and lights (e.g., light-emitting diodes). In one embodiment, the alarm triggers at a differential pressure of 5 mmHg. The alarm circuit 696 activates in one embodiment at flows greater than about 6 lpm (liters per minute).

In addition to the above circuits, a low pressure alarm circuit of certain embodiments is provided that includes a comparison circuit 647. The comparison circuit 647 includes a comparator U3B that receives the encoder input 604 and the pressure sensor input 602. The low pressure alarm circuitry compares the pressure sensor input 602 to one half of the encoder input 604 voltage. If the pressure sensor input 602 is lower than one half the encoder input 604 voltage for a significant amount of time, an alarm in the alarm circuit 696 turns on. The alarm of the alarm circuit 696 can be turned off much faster than it can be turned on in one implementation, due to the asymmetrical time constant of an integrator including a resistor R14 and a capacitor C2, which filters the pressure sensor input 602. In other embodiments, a value other than one half is used by the comparison circuit 647.

During normal operation, when the pressure sensor input 602 has stabilized at the encoder input 604 the user has selected, the integrator, using a resistor R14 and capacitor C2, charges up to the pressure sensor input 602 voltage in less than one second through resistor R53 and diode D1. If the suction load were to be suddenly removed and the pressure sensor input 602 dropped to zero, the integrator would slowly discharge through resistors R14 and R53. It could take up to 3 minutes in one embodiment for the integrator to discharge to less than one half of the encoder input 604 voltage, which would cause the comparison circuit 647 to output high and turn on the alarm.

The integrator time constant while charging, equal in one embodiment to the value of resistor R14 times capacitor C2, is 0.22 seconds until the pressure sensor input 602 is less than about one diode drop across diode D1 greater than the integrator voltage, when it becomes 66 seconds. This difference occurs because diode D1 stops conducting when the voltage across it is less than about one diode drop.

Example times it can take to turn the alarm on, listed in Table 2 below, assumes the pressure sensor input 602 has been stable at the indicated encoder input 604 value for several minutes, and that the pressure goes to zero nearly instantly. These assumptions may not apply or may be different in some embodiments.

TABLE 2

Low pressure alarm activation pressures and time to activate

| knob (mmHg) | alarm ON (mmHg) | alarm OFF (mmHg) | Time to alarm on from encoder input value to zero pressure (in seconds) |
|---|---|---|---|
| 200 | 76 | 82 | 64 |
| 180 | 69 | 71 | 64 |
| 160 | 61 | 65 | 66 |
| 140 | 50 | 55 | 68 |
| 120 | 42 | 46 | 70 |
| 100 | 33 | 37 | 74 |
| 90 | 28 | 32 | 77 |
| 80 | 24 | 28 | 80 |
| 70 | 19 | 24 | 84 |
| 60 | 15 | 20 | 91 |
| 50 | 10 | 14 | 102 |
| 40 | 7 | 11 | 124 |

Another circuit, a high pressure cutoff circuit, can also be provided. The high pressure cutoff circuit includes a comparison circuit 649, which in turn includes a comparator U12B. The comparison circuit 649 can remove electrical power from both pump motors 640 when the pressure from the second, backup pressure sensor 662 is higher than a fixed threshold. This circuit 649 can override all other pump power control because pump power is routed directly through a relay U14 that overrides the pump motors 640. The voltage from the second pressure sensor 662 can be low pass filtered by resistor R32 and capacitor C12. When the second pressure sensor 662 input reaches or exceeds 217 mmHg, power is removed from both pump motors 640 and does not return until the second pressure sensor 662 input falls below 212 mmHg. The comparator U12B of certain embodiments is active-low. When high, it turns on the relay U14 and allows power to reach the pump motors 640. When low, the relay U14 is turned off and power is disconnected from the pump motors 640.

In certain embodiments the high pressure cutoff circuit can be used as a redundant safety feature. Thus, the high pressure cutoff circuit may cut power to the pump motors 640 only when one or more components in the vacuum pump circuit 600 fails. Thus, for example, if a transistor or op amp in the pressure control circuit 601 fails, the high pressure cutoff circuit can cut power to the pump motors 640.

An intermittent delay circuit 645 is also provided that can change the overall duty cycle of the entire suction pump motors 640 from about 100% to about % 60, or to another desired percentage. The intermittent delay circuit 645 can accomplish this by periodically shorting the encoder input 604 wiper to ground, effectively telling the pressure control circuit 601 that the desired pressure is zero. After a delay of about 16 seconds, the wiper is released from ground, returning to whatever input value the user has selected for a delay of about 32 seconds. This cycle can repeat indefinitely as long as intermittent mode is selected. Other values for the delay values can be selected.

In one embodiment, the resistors R37 and R38 and the capacitor C23 set the on time ($T_{on}$) and off time ($T_{off}$) of the intermittent circuit 645, according to the following expressions:

$$T_{on}=0.693(R37+R38)*C23 \quad (2)$$

$$T_{off}=0.693(R38)*C23. \quad (3)$$

In certain embodiments, a pump soft start circuit 651 is also provided that prevents the pump motors 640 from running at 100% duty cycle during power up, since 100% duty cycle could draw significant current from the power supply, which could cause the power supply to enter overcurrent shutdown.

At startup, a capacitor C5 of the pump soft start circuit 651 is discharged. This can mean that the gate of transistor Q2 is 5 volts, which can mean that transistor Q2 is turned on, which in turn shunts the comparator U13B of the pulse width modulator 614 to ground through three diode drops. At this point, the pulse width modulator 614 input can be limited to three diode drops above ground (e.g., common), which effectively prevents the pulse width modulator 614 from outputting a high duty cycle to the pump motors 640. As capacitor C5 charges, the voltage across it increases, which means the voltage at the gate of the transistor Q2 continues to fall until the transistor Q2 turns off, removing the limit from the input of the pulse width modulator 614. The limit remains in effect for about 500 ms (milliseconds) in one embodiment.

Additionally, a mute circuit 653 is provided to allow the user to silence the audible alarm circuit 696 for a preset, fixed amount of time. The output of the mute circuit 653 controls transistor Q17, which controls U6, which is a 555 timer that controls the piezoelectric buzzer. When the output of the mute circuit 653 is 5 volts, the transistor Q17 is turned on, which enables the 555 timer U6 to be turned on by an alarm. This in turn means that the buzzer can turn on. When the output of the mute circuit 653 is 0 volts, the transistor Q17 is off and no power can reach the 555 timer U6. As a result, no power can reach the buzzer.

A mute button can be provided on the front panel of the vacuum pump, which can be a momentary switch or the like. The switch can connect 5 volts to resistor R62 when depressed. Activating the switch charges up capacitor C22 to 5 volts in about 100 ms. When the mute button is released, the capacitor C22 slowly discharges through the resistor R31. The comparator U16 compares the voltage across the capacitor C22 to a threshold of 1.47 volts, provided by a voltage divider of resistors R64 and R63.

The time the mute circuit 653 remains active is controlled by the voltage divider R64 and R63, by the capacitor C22, and by the resistor R31. In one embodiment, the values of the capacitor C22 and the resistor R31 can be chosen so that the mute time can be set from between 0 and 354 seconds by varying the resistors R64 and R63, e.g., by using user-controlled potentiometers for the resistors R64, R63. The time the mute function remains active can be expressed as:

$$t=R31*C22*\ln(5/V_{div}), \quad (4)$$

where $V_{div}$ is the voltage of the R64/R63 voltage divider.

Moreover, a low voltage alarm circuit 657 can be provided that activates when the +12 volt supply, either from a battery, AC adapter, or DC in jack, falls below about 10V. It can include a simple comparator U3A which compares one fourth of the +12 voltage rail to a fixed threshold of 2.5 volts. The output is active at 5 volts and drives transistors (e.g., MOSFETs) which control the beeper and alarm circuit 696.

Based on the foregoing description, one can see that providing pressure control without using a processor provides significant advantages over existing systems. In particular, reduced cost, increased safety, and a less-complex FDA approval process are some advantages provided by certain embodiments described herein.

In addition to the components and features described herein, the embodiments of the negative pressure wound therapy apparatus described herein can have any of the features and components that are known in the art or that are suitable for such system. The EZCARE Negative Pressure System User Guide available from Smith & Nephew is hereby incorporated by reference. The pressure control circuitry described herein can be configured to be used with any negative pressure wound therapy apparatus currently available or later developed.

While the above detailed description has shown, described, and pointed out novel features as applied to various embodiments, it will be understood that various omissions, substitutions, and changes in the form and details of the device or process illustrated may be made without departing from the spirit of the disclosure. Additionally, the various features and processes described above may be used independently of one another, or may be combined in various ways. All possible combinations and subcombinations are intended to fall within the scope of this disclosure.

As will be recognized, certain embodiments described herein may be embodied within a form that does not provide all of the features and benefits set forth herein, as some features may be used or practiced separately from others. The scope of the inventions is indicated by the appended claims rather than by the foregoing description. All changes which come within the meaning and range of equivalency of the claims are to be embraced within their scope.

What is claimed is:

1. An apparatus for detecting high air flow in a negative pressure wound therapy system, comprising:
   a wound dressing;
   a fluid collection container;
   a vacuum pump;
   a plurality of lumens configured to at least channel a flow of fluid between said wound dressing, said fluid collection container, and said pump;
   a flow restrictor configured to restrict flow of fluid in a lumen of the plurality of lumens;
   a first pressure sensor configured to measure a pressure along a lumen on a first side of said flow restrictor and to generate a first output signal;
   a second pressure sensor configured to measure a pressure along a lumen on a second side of said flow restrictor apart from said first side and to generate a second output signal;
   a difference circuit configured to provide a difference signal reflecting a difference between the first and second output signals;
   a comparison circuit configured to compare the difference signal with a threshold corresponding to a high flow rate and to provide a comparison; and
   an alarm circuit configured to produce an alarm responsive to the comparison, the alarm reflecting a high flow condition.

2. The apparatus of claim 1, further comprising an integrator circuit interposed between the difference circuit and the comparison circuit, the integrator circuit configured to introduce a delay into the difference signal.

3. The apparatus of claim 1, further comprising a filter configured to reduce noise in the difference signal.

4. The apparatus of claim 1, wherein the alarm circuit is configured to produce the alarm when the comparison indicates that the difference signal exceeds the threshold.

5. The apparatus of claim 1, wherein the difference circuit comprises a comparator.

6. The apparatus of claim 1, wherein the difference circuit comprises an amplifier.

7. The apparatus of claim 1, wherein the flow restrictor comprises an orifice.

8. The apparatus of claim 1, wherein the threshold comprises a threshold signal and the comparison comprises a comparison signal.

9. The apparatus of claim 1, wherein the threshold is equal to or greater than 7.5 mmHg.

10. The apparatus of claim 1, wherein the comparison circuit is a different circuit than the difference circuit.

11. The apparatus of claim 1, wherein the flow restrictor is configured to restrict flow of fluid in the lumen between the fluid collection container and the pump.

12. The apparatus of claim 1, wherein the first and second pressure sensors are configured to measure the pressure along the same lumen as the lumen where the flow restrictor is configured to restrict flow of fluid.

13. The apparatus of claim 1, wherein the threshold is equal to or greater than 5 mmHg.

14. The apparatus of claim 1, wherein the threshold is equal to or greater than 10 mmHg.

15. A method for treating a wound, comprising:
   placing a wound dressing over the wound to form a substantially fluid tight seal;
   providing a fluid flow path between the wound dressing, a fluid collection container, and a pump;
   applying negative pressure to the wound dressing;
   restricting a movement of fluid in a portion of the fluid flow path with a flow restrictor;
   measuring pressure at a first location in the portion of the fluid flow path where the movement of fluid is restricted and at a second location in the portion of the fluid flow path where the movement of fluid is restricted, wherein the first location is on a first side of the flow restrictor and the second location is on a second side of the flow restrictor apart from said first side;
   determining a difference between the measured pressure at the first location and the second location; and
   comparing the difference to a threshold corresponding to a high flow rate and generating an alarm when the difference is determined to exceed the threshold.

16. The method of claim 15, wherein the alarm indicates a leak in the fluid flow path.

17. The method of claim 15, further comprising determining a flow rate in at least a portion of the fluid flow path based at least in part on the difference.

18. The method of claim 17, wherein determining the flow rate comprises integrating the difference.

19. The method of claim 17, further comprising displaying the flow rate.

20. The method of claim 15, further comprising filtering the difference before comparing the difference to the threshold.

21. The method of claim 15, wherein the flow restrictor comprises a lumen.

22. The method of claim 15, wherein the flow restrictor comprises an orifice.

23. The method of claim 15, wherein the threshold is equal to or greater than 7.5 mmHg.

24. The method of claim 15, wherein the threshold is equal to or greater than 5 mmHg.

25. The method of claim 15, wherein the threshold is equal to or greater than 10 mmHg.

* * * * *